US 12,251,079 B2

United States Patent
Lalli et al.

(10) Patent No.: US 12,251,079 B2
(45) Date of Patent: Mar. 18, 2025

(54) APPLICATOR AND SLEEVE ACCESSORY FOR A SPECULUM AND USE THEREOF

(71) Applicant: CEEK Women's Health, Inc., Portland, OR (US)

(72) Inventors: Maria Lalli, Portland, OR (US); Christian Freissler, Portland, OR (US); Katie Lee, Portland, OR (US); Ute Peppersack, Portland (CA)

(73) Assignee: CEEK WOMEN'S HEALTH, INC., Portland, OR (US)

( * ) Notice: Subject to any disclaimer, the term of this patent is extended or adjusted under 35 U.S.C. 154(b) by 636 days.

(21) Appl. No.: 17/284,412

(22) PCT Filed: Oct. 9, 2019

(86) PCT No.: PCT/US2019/055422
§ 371 (c)(1),
(2) Date: Apr. 9, 2021

(87) PCT Pub. No.: WO2020/076967
PCT Pub. Date: Apr. 16, 2020

(65) Prior Publication Data
US 2022/0000345 A1    Jan. 6, 2022

Related U.S. Application Data

(60) Provisional application No. 62/744,544, filed on Oct. 11, 2018.

(51) Int. Cl.
*A61B 1/00* (2006.01)
*A61B 1/32* (2006.01)

(52) U.S. Cl.
CPC ...... *A61B 1/00135* (2013.01); *A61B 1/00103* (2013.01); *A61B 1/32* (2013.01)

(58) Field of Classification Search
CPC ... A61B 1/32; A61B 1/00135; A61B 1/00103; A61B 1/303; A61B 1/00137
See application file for complete search history.

(56) References Cited

U.S. PATENT DOCUMENTS 2,797,684 A    7/1957  Moore
3,841,317 A *  10/1974 Awais ................ A61B 1/00142
                                                  600/203

(Continued)

FOREIGN PATENT DOCUMENTS

EP    0966223 A1    12/1999
EP    1833376 A2    9/2007

(Continued)

OTHER PUBLICATIONS

International Search Report and Written Opinion for Application No. PCT/US2016/069047, mailed on Jul. 11, 2017, 16 pages.

(Continued)

*Primary Examiner* — Ellen C Hammond
*Assistant Examiner* — Holly Joanna Lane
(74) *Attorney, Agent, or Firm* — Mintz, Levin, Cohn, Ferris, Glovsky and Popeo, P.C.

(57) ABSTRACT

An applicator for positioning a sleeve accessory on medical speculum, and a method for using the applicator, is provided. The applicator has a flat, oblong shape with a distal end and a proximal end, the proximal end being broader than the distal end. The distal end of the applicator includes a first prong and a second prong. At least a portion of the distal end of the applicator is configured to slide into a lumen of a sleeve accessory to facilitate positioning of the sleeve accessory on a medical speculum.

17 Claims, 31 Drawing Sheets

(56) References Cited

U.S. PATENT DOCUMENTS

| | | | |
|---|---|---|---|
| 4,492,220 A | 1/1985 | Hayes | |
| 4,984,564 A | 1/1991 | Yuen | |
| 5,007,409 A | 4/1991 | Pope | |
| 5,072,720 A | 12/1991 | Francis et al. | |
| 5,179,936 A | 1/1993 | Ohara et al. | |
| 5,342,385 A | 8/1994 | Norelli et al. | |
| 5,460,165 A | 10/1995 | Mayes | |
| 5,598,852 A | 2/1997 | Spery | |
| 5,716,329 A | 2/1998 | Dieter | |
| 5,823,008 A | 10/1998 | Nikai et al. | |
| 5,865,729 A | 2/1999 | Meehan et al. | |
| 6,036,638 A * | 3/2000 | Nwawka | A61B 1/00142 600/220 |
| D445,895 S | 7/2001 | Svendsen | |
| 6,347,243 B1 | 2/2002 | Fraden | |
| 6,361,543 B1 | 3/2002 | Chin et al. | |
| 6,432,048 B1 * | 8/2002 | Francois | A61B 1/32 600/220 |
| D475,447 S | 6/2003 | Stout, Jr. | |
| D476,742 S | 7/2003 | Wilkinson | |
| D488,217 S | 4/2004 | Stout, Jr. | |
| D488,859 S | 4/2004 | Stout, Jr. | |
| 6,902,530 B1 * | 6/2005 | Pianka | A61B 1/00142 600/220 |
| 7,063,664 B2 * | 6/2006 | Mohajer | A61B 1/303 600/184 |
| 7,896,806 B2 | 3/2011 | Shah et al. | |
| D651,709 S | 1/2012 | Zeyfang | |
| D664,639 S | 7/2012 | Hoke et al. | |
| D736,372 S | 8/2015 | Anderson | |
| D745,347 S | 12/2015 | Gurwicz et al. | |
| D750,779 S | 3/2016 | Ahluwalia et al. | |
| D751,198 S | 3/2016 | Ahluwalia et al. | |
| D768,293 S | 10/2016 | Sawicki et al. | |
| D779,665 S | 2/2017 | Hasbun | |
| D785,166 S | 4/2017 | Sawicki et al. | |
| D796,669 S | 9/2017 | Palmer | |
| D804,649 S | 12/2017 | Perry | |
| D817,124 S | 5/2018 | Gurwicz et al. | |
| D820,441 S | 6/2018 | Ketelhohn et al. | |
| D842,991 S | 3/2019 | Cable, Jr. | |
| D869,653 S | 12/2019 | Klaassen | |
| 2003/0069477 A1 | 4/2003 | Raisman et al. | |
| 2004/0231772 A1 | 11/2004 | Leonard et al. | |
| 2005/0021080 A1 | 1/2005 | Feuer et al. | |
| 2005/0124860 A1 | 6/2005 | Mohajer | |
| 2005/0192482 A1 | 9/2005 | Carpenter et al. | |
| 2006/0079924 A1 | 4/2006 | Sanders et al. | |
| 2006/0084843 A1 | 4/2006 | Sommerich et al. | |
| 2006/0224043 A1 | 10/2006 | Guinan | |
| 2008/0114210 A1 * | 5/2008 | Shah | A61B 1/32 264/80 |
| 2008/0242938 A1 | 10/2008 | Larkin | |
| 2009/0062691 A1 | 3/2009 | Kim | |
| 2009/0099422 A1 | 4/2009 | George | |
| 2016/0029882 A1 | 2/2016 | Young | |
| 2017/0181607 A1 | 6/2017 | Lalli et al. | |
| 2018/0200079 A1 * | 7/2018 | Eastlack | A61B 17/025 |
| 2018/0317746 A1 | 11/2018 | Lalli et al. | |
| 2019/0082948 A1 * | 3/2019 | Ford | A61B 1/32 |

FOREIGN PATENT DOCUMENTS

| | | |
|---|---|---|
| WO | 9612437 A1 | 5/1996 |
| WO | 9833431 A1 | 8/1998 |
| WO | 2006064247 A2 | 6/2006 |
| WO | 2011024901 A1 | 3/2011 |

OTHER PUBLICATIONS

International Search Report and Written Opinion received for Application No. PCT/US2018/031202, mailed on Aug. 17, 2018, 8 pages.

International Search Report and Written Opinion received for Application No. PCT/US2019/055422, mailed on Dec. 16, 2019, 9 pages.

International Search Report and Written Opinion received for PCT Application No. PCT/US2016/069048, mailed on Jul. 11, 2017, 16 pages.

* cited by examiner

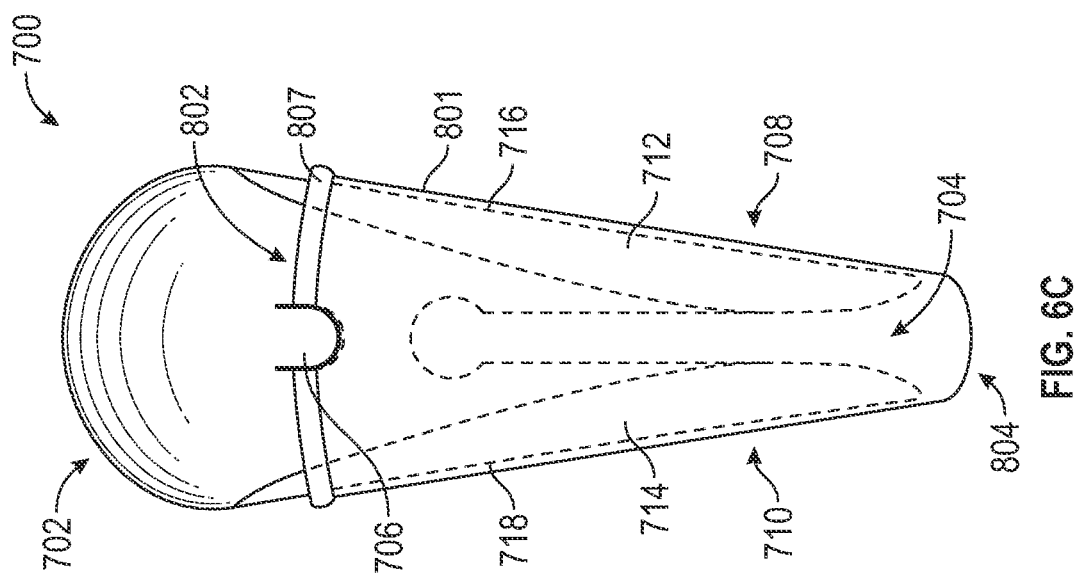

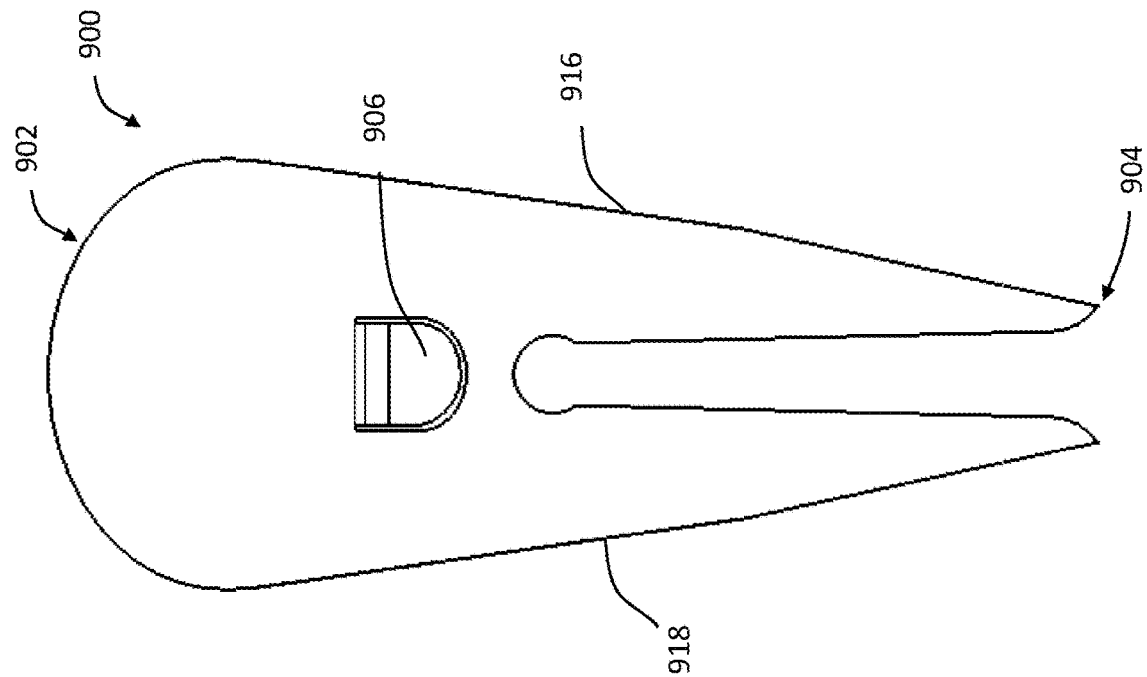
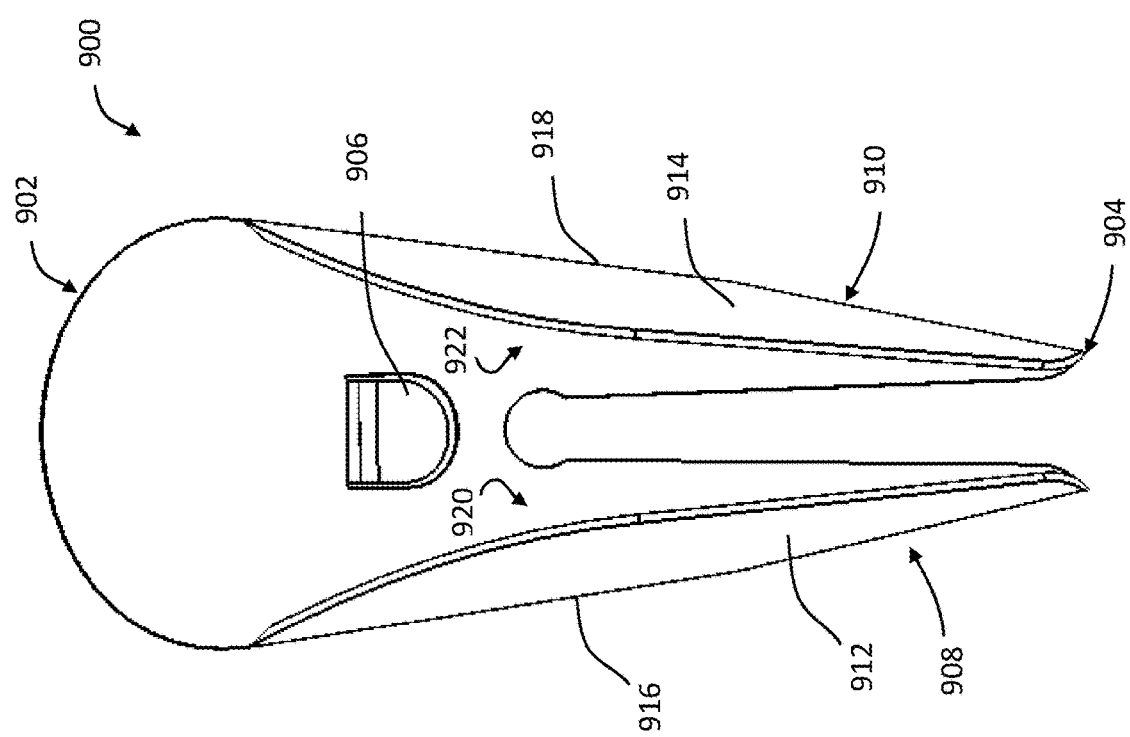

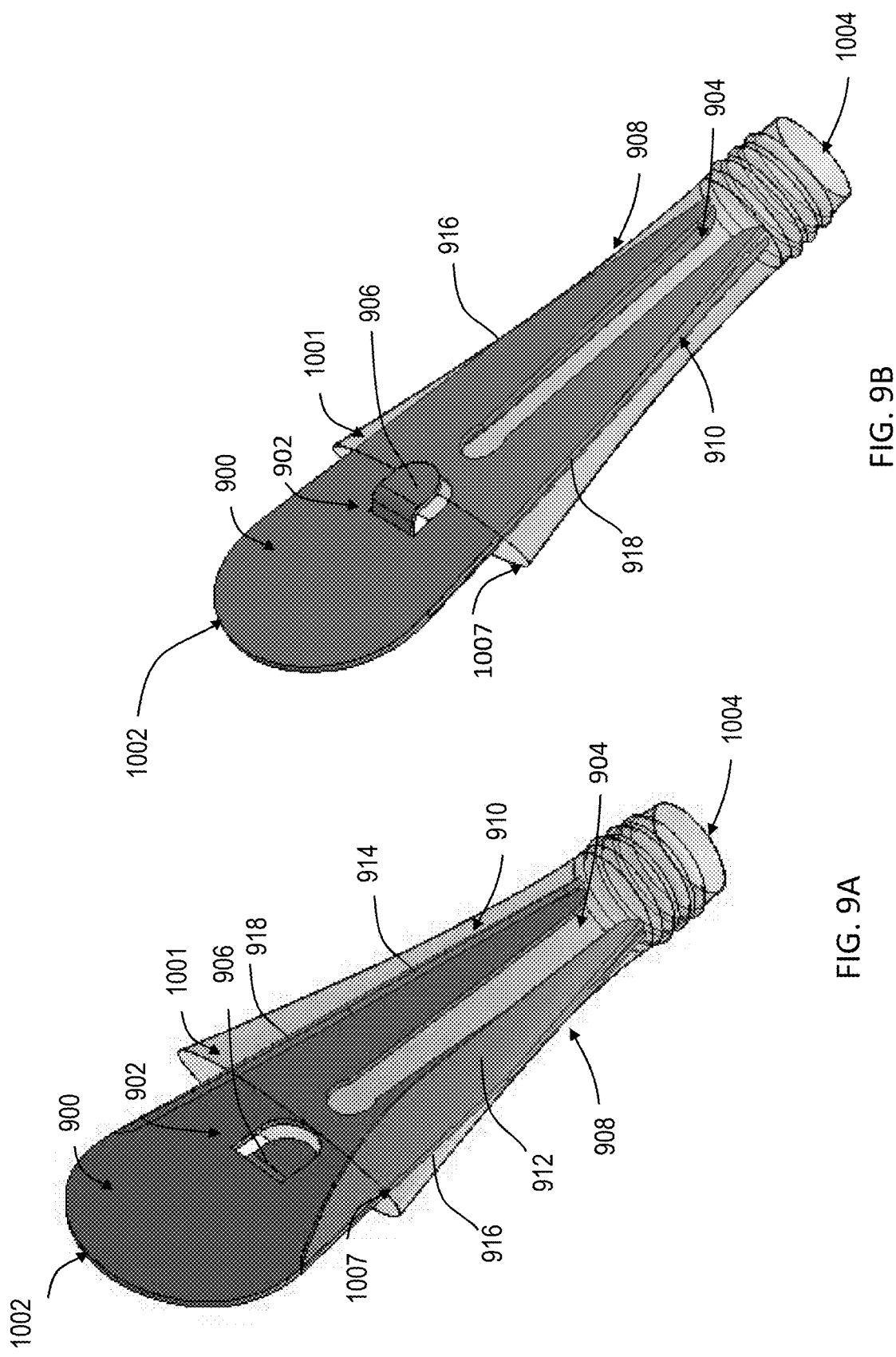

APPLICATOR AND SLEEVE ACCESSORY FOR A SPECULUM AND USE THEREOF

CROSS-REFERENCE TO RELATED APPLICATIONS

The present application is a National Stage Entry of International Application No. PCT/US2019/055422, filed Oct. 9, 2019, entitled APPLICATOR AND SLEEVE ACCESSORY FOR A SPECULUM AND USE THEREOF, which claims priority to U.S. Patent Application No. 62/744,544, filed Oct. 11, 2018, entitled APPLICATOR AND SLEEVE ACCESSORY FOR A SPECULUM AND USE THEREOF, the disclosure of each of which is incorporate herein by reference in its entirety.

FIELD

The present invention relates generally to the field of a medical speculum, and more particularly to an applicator for applying a sleeve to a medical speculum.

BACKGROUND

A speculum is a medical tool used to provide visualization into a body cavity. Speculums or specula are traditionally used for viewing and accessing the vaginal cavity for gynecology patients. The traditional speculum consists of two blades with a hinge and a handle. The blades are inserted into the body cavity in a closed position, and separated by squeezing two pieces of the handle together or applying force to a lever attached to the handle, thereby dilating the vagina and providing visualization of and accessibility to the vagina, the cervix, and surrounding areas. Once opened, the speculum can be locked in an open position, e.g., by using a screw-based mechanism so an operator (e.g., physician, nurse, mid-wife, etc.) does not need to continue squeezing the pieces of the handle or the lever during the inspection. The operator can then proceed with inspecting the vagina, conducting a Pap smear, or any other medical procedures that may need to be provided.

The double blade design of speculum devices has been in use since the 1800s, and few changes have been made to the original design. The biggest changes with the double-blade design have been changes in the material from metal to plastic and the addition of internal lighting on some models of the speculum so that the operator does not have to rely on external lighting to gain a clear view of the vagina and the cervix.

There are drawbacks with the traditional two blade design. For one, tissue can enter between the blades once they are opened inside the vaginal cavity, a common occurrence that providers characterize as "side wall encroachment." Women, especially obese women, women with multiple vaginal births, or those with vaginal laxity, may have extra tissue in the side walls of the vagina that may fall into the space between the two blades once opened. This can cause problems for operators, particularly in providing clear visualization of the vagina and cervix, which potentially limits the effectiveness of the procedure. Furthermore, with all patients, when trying to close the speculum blades, tissue and/or pubic hair may become pinched between the blades. Pinching is extremely painful for patients and difficult for the operator to avoid without removing the speculum in an open position, which causes significant discomfort to the patients as well. There are no satisfactory solutions for these problems, resulting in tremendous patient discomfort with the entire speculum experience.

In an attempt to limit sidewall encroachment and allow for better visualization of the vaginal walls and cervix, operators may attempt to place condoms or portions of medical gloves over the speculum. This is an unsatisfactory and ineffective approach as condoms and gloves were not designed to support the internal pressure of the vaginal walls, but to be as thin as possible. Furthermore, using these solutions can result in both condoms and glove fingers, or torn portions of them, being left behind in the vaginal cavity following removal of the speculum. Alternatively, operators may choose to use larger speculums to provide a larger viewing/accessing window to compensate for tissue entering the side of the speculum between the blades. However, increasing the size of the speculum can provide discomfort to patients. Moreover, while there are now different sizes of speculums offered for an examination, it can be hard to determine the correct size for a patient as the size of the patient does not necessarily correlate with the size of the speculum that should be used.

An additional drawback to the traditional speculum design is that speculums are traditionally made of metal, though some made with disposable plastic have been increasing in use. When the speculum is made of metal, it can feel cold to the patient upon entry to the vaginal cavity, especially in comparison to the internal temperatures of the body, which can result in discomfort for the patient during the procedure. This may result in the patient tensing up and making the procedure more painful. Even when made of plastic, the design of the speculum is generally the same as the traditional design (but for some differences that may exist in the locking mechanisms, wall thicknesses, consistencies between the types of plastic, etc.), meaning that even plastic speculums may face some of the same drawbacks as traditional speculums.

Embodiments herein generally relate to applicators for accessories to improve speculum devices, components of the same, and methods of making and using the same. The accessories overcome many drawbacks of existing speculum devices, and the applicators enable practitioners to easily position the accessories on speculum devices for use during a medical procedure. In one aspect, an applicator is provided for easy positioning of a sleeve accessory, either on an existing speculum design or an updated speculum design, to cover an insertion portion of the speculum.

SUMMARY

One embodiment relates to an applicator for positioning a sleeve accessory on a medical speculum. The applicator has a flat, oblong shape with a distal end and a proximal end, the proximal end being broader than the distal end. Additionally, the distal end includes a first prong and a second prong. At least a portion of the distal end of the applicator is configured to slide into a lumen of a sleeve accessory to facilitate positioning of the sleeve accessory on a medical speculum.

In some embodiments, the first prong and the second prong are folded into a first pocket and a second pocket, respectively. The first pocket and the second pocket may receive the medical speculum and thereby guide the medical speculum into the lumen of the sleeve accessory. In some embodiments, the first prong and the second prong are spaced apart such that, once the applicator has been slid at least partially into the lumen of the sleeve accessory, the first prong and the second prong abut inner walls of the sleeve accessory. In some embodiments, the proximal end of the applicator includes a tab. The tab may be tucked over a proximal end of the sleeve accessory. In some embodiments, the applicator is made of a rubber, plastic, paper or cardboard material.

Another embodiment relates to a method for positioning a sleeve accessory on a medical speculum. The method includes providing a medical speculum with a pair of bills, providing a sleeve accessory having a cylindrical sleeve body defining a lumen, and providing an applicator having a flat, oblong shape with a distal end and a proximal end, the proximal end being broader than the distal end. The distal end of the applicator includes a first prong and a second prong. The first prong and the second prong are configured to be folded into a first pocket and a second pocket, respectively, the first pocket and the second pocket configured to receive the bills of the medical speculum. The method further includes positioning the lumen of the sleeve accessory about the distal end of the applicator, sliding the bills of the speculum between the first pocket and the second pocket of the applicator to position the bills of the speculum in the lumen of the sleeve accessory; and removing the applicator from the lumen of the sleeve accessory.

Another embodiment relates to a kit. The kit includes a sleeve accessory having a cylindrical sleeve body defining a lumen, wherein the sleeve accessory is configured to be positioned on an insertion portion of a medical speculum, and an applicator having a flat, oblong shape with a distal end and a proximal end, the proximal end being broader than the distal end. The distal end includes a first prong and a second prong. The applicator is configured to slide, by the distal end of the applicator, at least partially into the lumen of the sleeve accessory to facilitate positioning of the sleeve accessory on the insertion portion of the medical speculum.

Another embodiments relates to a sleeve accessory. The sleeve accessory may be positioned on a medical speculum. The sleeve accessory may include a sleeve body. The sleeve body defines a lumen that extends from a proximal end to a distal end of the sleeve body. The sleeve accessory is configured to be positioned on an insertion portion of the medical speculum. The sleeve body includes a flared portion and an elongated portion. The flared portion extends radially outwardly towards the proximal end of the sleeve body. The elongated portion extends from the flared portion towards the distal end of the sleeve body.

BRIEF DESCRIPTION OF THE DRAWINGS

FIG. 6C is a top view of the applicator of FIGS. 6A and 6B positioned in a sleeve accessory, according to an example embodiment.

FIG. 7E is a bottom view of the applicator of FIG. 7A, in a folded position, according to an example embodiment.

FIG. 7F is a top view of the applicator of FIG. 7A, in a folded position, according to an example embodiment.

FIG. 9A is a bottom perspective view of the applicator of FIGS. 7A-7F at least partially in the sleeve accessory of FIGS. 8A-8F, according to an example embodiment.

FIG. 9B is a top perspective view of the applicator of FIGS. 7A-7F at least partially in the sleeve accessory of FIGS. 8A-8F, according to an example embodiment.

DESCRIPTION

Figure 1:
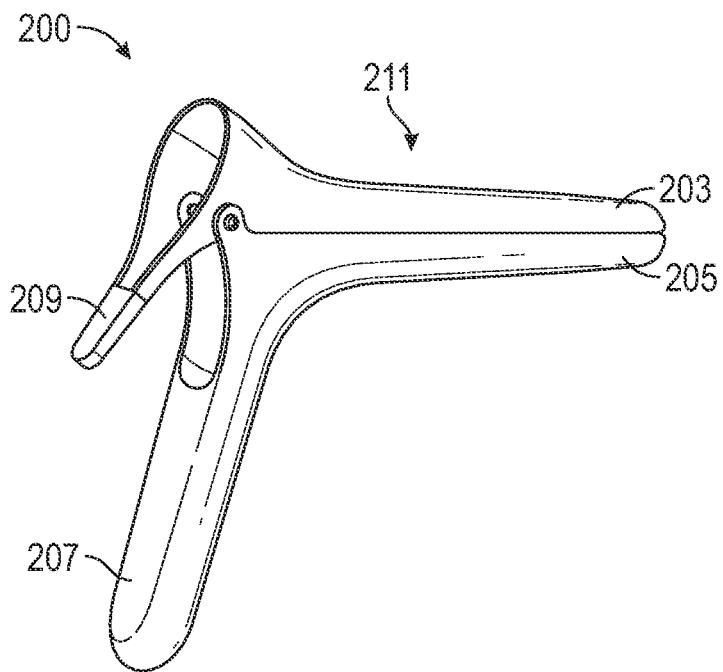
FIG. 1 is a side perspective view of a medical speculum on which a sleeve accessory according to various embodiments can be used.

In the following description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. The detailed description is intended as a description of exemplary embodiments and is not intended to represent the only embodiments which may be practiced. The term "exemplary," as used herein, means "serving as an example, instance, or illustration," and should not necessarily be construed as preferred or advantageous over other embodiments. Other embodiments may be utilized, and other changes may be made, without departing from the spirit or scope of the subject matter presented herein. It will be readily understood that the aspects of the present disclosure, as generally described herein and illustrated in the Figures, can be arranged, substituted, combined, and designed in a wide variety of different configurations, all of which are explicitly contemplated by and form part of this disclosure.

Referring to the Figures generally, an applicator for a sleeve accessory, or modifier sleeve, for a medical speculum is shown. The sleeve accessory may be used on any traditional speculum or any new or updated speculum design, including speculums that may be specifically designed for use with the sleeve accessory according to the present embodiments. The sleeve has an expandable body portion and is configured to be removably attached to an insertion portion of a speculum. In certain uses, a practitioner may be able to select a speculum with a narrower profile than the practitioner would regularly select because the sleeve reduces some of the previously described shortcomings of the traditional speculum design, for example, the problem of vaginal side wall tissue falling into the user's line of sight during use. The applicator is then used by the practitioner to easily and quickly position the sleeve accessory onto the bills of a speculum with minimal direct handling of the sleeve.

Referring now to FIG. 1, a two-blade speculum is shown according to certain traditional designs. As shown, the speculum 200 has an upper bill 203 and a lower bill 205, a handle 207, and a lever 209. The upper bill 203 and the lower bill 205 together comprise an elongated insertion portion 211. The insertion portion 211, which is expandable as described herein, may be inserted into the vaginal cavity of a female patient. During insertion, the upper bill 203 and the lower bill 205 are in a closed position, wherein there is a minimal amount of space between the two bills. Once inserted and in order to dilate the vaginal cavity, the bills 203 and 205 are separated into an open position by pressing the lever 209 towards the handle 207. In accordance with typical speculum designs, the speculum 200 may be made of any sturdy biomaterial including metals and plastics.

Figure 2:
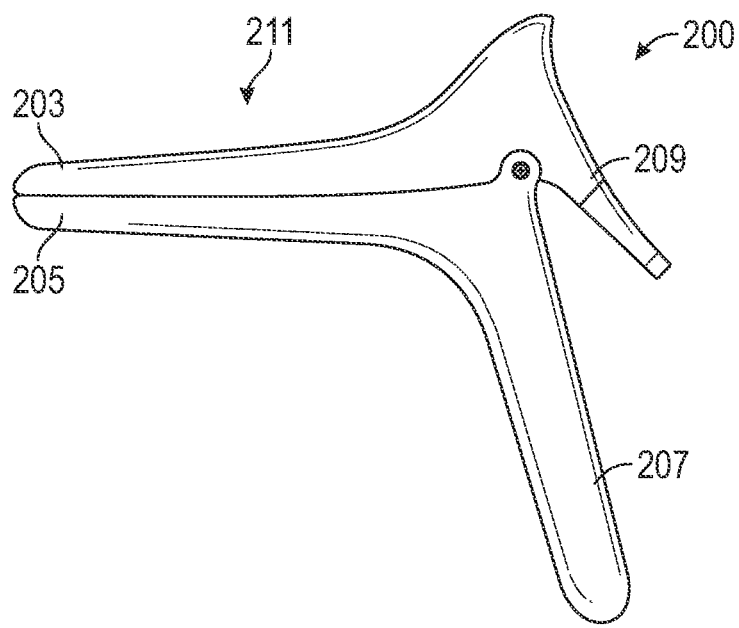
FIG. 2 is a side view of the medical speculum of FIG. 1.

Referring now to FIG. 2, a side view of speculum 200 is shown. The upper bill 203 and the lower bill 205 may be configured in such a way that when in the closed position, the upper bill 203 and the lower bill 205 are wider near the handle 207 than near a body or end of the insertion portion 211, i.e., the bills 203 and 205 distend quickly to create somewhat of a cone shape near the handle 207, as shown in the side view of FIG. 2. The bills 203 and 205 may maintain a constant shape after the cone, forming the elongated insertion portion 211. The upper bill 203 and the lower bill 205 of the elongated insertion portion 211 may have a uniform width or diameter as the bills 203 and 205 extend away from the handle 207. In other embodiments, the proximal portion of the bills 203 and 205 near the handle 207 may be up to two times wider than the distal end of the bills 203 and 205.

At a distal end of the elongated insertion portion 211, away from the proximal handle 207, the bills 203 and 205 may be rounded (e.g., the bills 203 and 205 may each be rounded, the ends of bills 203 and 205 closed together may form a rounded end, etc.). A rounded end may provide more comfort to a patient while receiving the speculum 200 in a cavity. The bills 203 and 205 may also be configured such that when in the closed position, the ends the bills 203 and 205 do not abut one another, creating a gap which helps to prevent tissue from becoming lodged in between the bills 203 and 205. In one embodiment, the bills 203 and 205 may be of the same length such that when the bills 203 and 205 are closed, they form a smooth, continuous end to the insertion portion 211. Alternatively, in another embodiment, one of the bills 203 and 205 may be longer than the other, such that when the bills 203 and 205 are in the closed position, the longer bill juts out from beneath or above the other bill.

As shown in FIG. 2, the handle 207 includes an upper portion and a lower portion. The upper portion of the handle 207 is coupled to bills 203 and 205. The lower portion provides a location for the user to hold the speculum 200. Coupled to the handle 207 is the lever 209. The lever 209 includes a mechanism for opening and closing bills 203 and 205. While the lever 209 is shown to be coupled to the upper portion of the handle 207, the lever 209 may be coupled to the handle 207 at any location. In some embodiments, the speculum 200 may also include a mechanism for locking the bills 203 and 205 into an open position.

Figure 3:
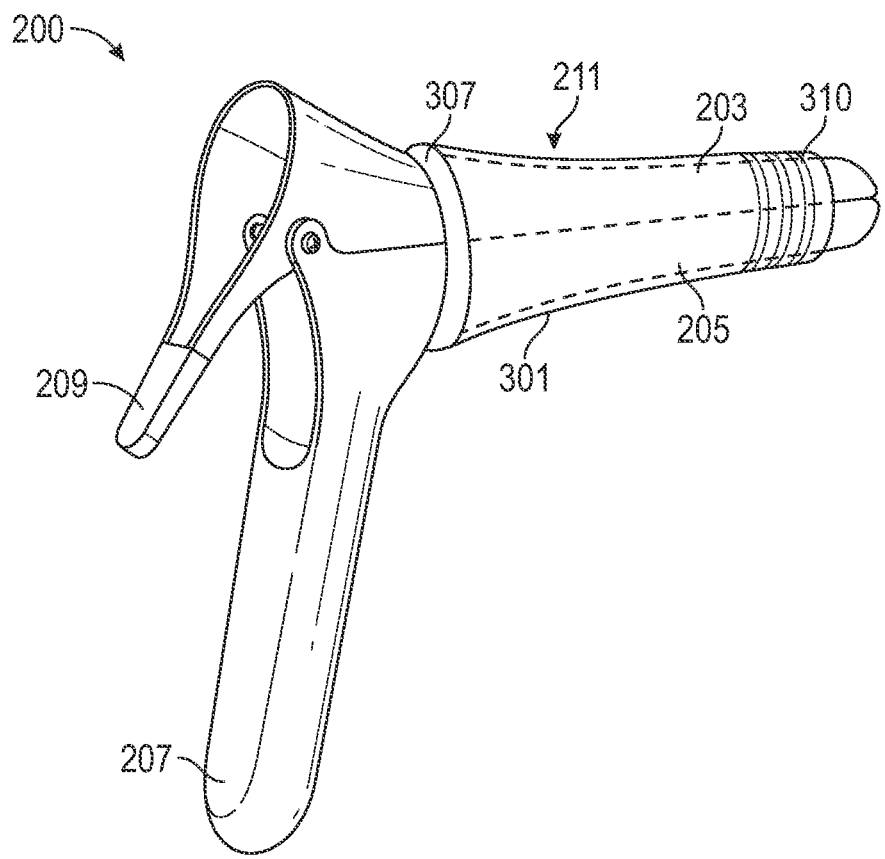
FIG. 3 is a side perspective view of a sleeve accessory positioned on a medical speculum, according to an example embodiment.

As described herein, using a sleeve accessory, such as sleeve accessory 301 shown in FIG. 3, with a medical speculum, such as speculum 200, may overcome the previously described shortcomings of the traditional speculum in a variety of ways. First, the sleeve may be made of a rubber or other soft material that is warmer than the traditional metal speculum bills. As such, inserting a speculum with a sleeve accessory attached may be less shocking, and thus more comfortable, to a patient than a bare metal speculum. The material may be at least substantially transparent to allow for good visualization of the vaginal cavity through the speculum with attached sleeve. Furthermore, a slimmer profile speculum can be utilized because of the sleeve (e.g., because the sleeve allows for improved visualization such that a larger speculum is not necessary), which provides better comfort for the patient during the procedure, examination, or surgery involving the speculum. The sleeve moreover allows the speculum to be removed in a closed position while preventing the pinching of either tissues or pubic hair during the process, significantly improving patient comfort while reducing patient anxiety. Importantly, the sleeve also provides the side wall support between the upper bill and the lower bill of the speculum that allows the practitioner better and less impeded visualization into the vagina and cervix. When used during an electrosurgery procedure, the sleeve accessory may additionally provide insulation to protect the vaginal walls of a patient during the electrosurgery procedure. Accordingly, using a sleeve accessory with a medical speculum may provide a number of benefits to the patient. Because of this, it would also be advantageous to practitioners to have an applicator tool to help them in quickly and correctly positioning a sleeve accessory on a medical speculum. A sleeve accessory may be the same or similar to those described in U.S. patent application Ser. No. 15/393,041 filed Dec. 28, 2016, which is incorporated by reference herein in its entirety.

Though specific reference is made in this specification to the elements or features of speculum 200, it is understood that the accessory or modifier elements described herein, as well as any applicators for the accessory or modifier elements described herein, may be used with any speculum having an elongated and expandable insertion portion, such as any two-blade speculum design. The features herein used to describe speculum 200 may also be present on any other speculum on which the accessory or modifier elements described herein may be used.

In one aspect, a practitioner may use a sleeve accessory adapted to be used with a speculum, such as speculum 200, as follows. First, a user positions a sleeve accessory on an insertion portion of a speculum, such as insertion portion 211 on speculum 200, while the speculum is in a closed position. In exemplary embodiments, the user positions the sleeve accessory on the insertion portion by using an applicator tool, such as the applicators described herein, which aids the practitioner in quickly and correctly positioning the sleeve accessory on the insertion portion of the speculum. The user then inserts the speculum with the attached sleeve accessory into a patient's vagina. The user sets the speculum to the open position, thereby separating bills of the insertion portion and stretching the sleeve accessory. Next, the user performs a medical procedure on the patient using the speculum in the open position. The medical procedure may be any obstetric or gynecological procedure, such as an examination of the vaginal cavity, a Pap smear, an insertion or removal of an intrauterine device (IUD), an insemination, a sexually transmitted infection (STI) testing, a tissue collection, a biopsy, or an electrosurgery procedure. After the user completes the medical procedure, the user closes the speculum and removes the speculum from the patient. Finally, the user removes the sleeve accessory from the speculum (e.g., by rolling the sleeve accessory off, by using a removal device, etc.).

Figure 4:
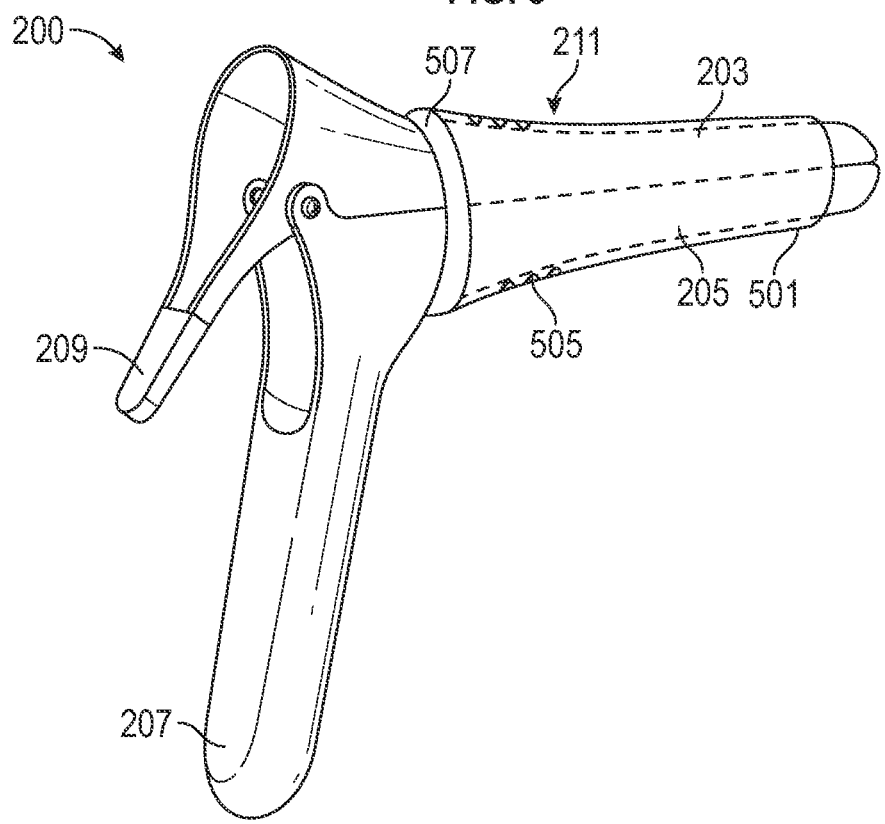
FIG. 4 is a side view of a sleeve accessory positioned on a medical speculum, according to an example embodiment.
Figure 5:
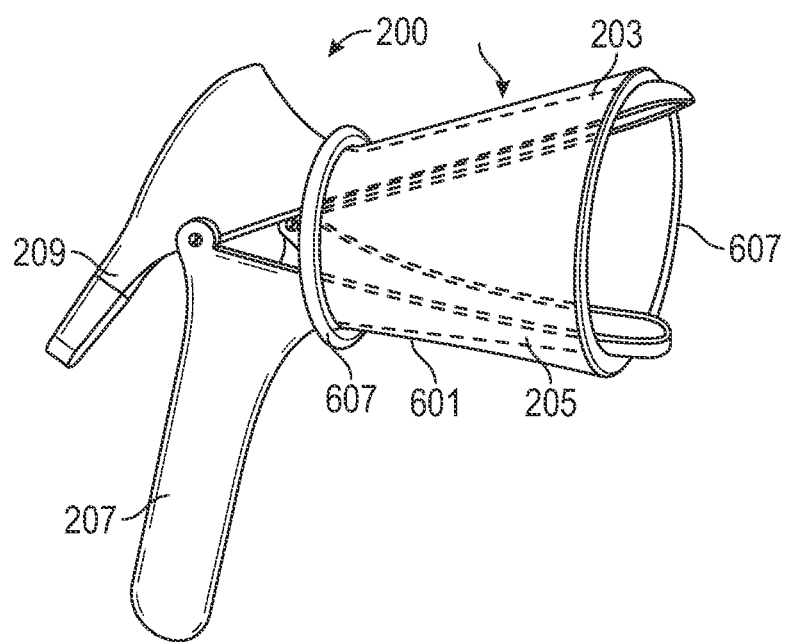
FIG. 5 is a side perspective view of a sleeve accessory positioned on a medical speculum in an open position, according to an example embodiment.

FIGS. 3-5 show examples of a sleeve accessory to be used with a speculum. The sleeve accessory may be the same or similar to those described in U.S. patent application Ser. No. 15/393,041 filed Dec. 28, 2016, which is incorporated by reference herein in its entirety. FIG. 3 depicts a sleeve accessory 301 on the elongated insertion portion 211 of speculum 200. As shown, the sleeve accessory 301 is configured to be positioned on the elongated insertion portion 211, to surround or enclose both bills 203 and 205, while the bills are in a closed position. In some embodiments, the sleeve accessory 301 has a cylindrical sleeve body. By "cylindrical" it is meant that the sleeve body has a continuous, longitudinal shape that surrounds a hollow area (e.g., a lumen or hollow sleeve channel) within an inner wall or surface of the cylinder. The cylindrical sleeve body is not limited to a circular cylinder and may instead have a cross-sectional shape that is a square, a rectangle, a circle, an oval, a triangle, and so on. In the embodiment shown, the sleeve accessory 301 has a cylindrical shape with a proximal opening through which the insertion portion 211 can be inserted. In the embodiment shown, the shape of the sleeve accessory 301 substantially matches the shape of the bills, or may be in another shape, on which the sleeve accessory 301 is being positioned. As such, the cylindrical body of the sleeve accessory 301 may have a uniform width or diameter between a distal end of the sleeve body and a proximal end of the sleeve body while the sleeve accessory 301 is in an un-stretched or unexpanded state, to match a uniform width or diameter of the bills 203 and 205 extending away from the handle 207. In one embodiment, the uniform diameter of the cylindrical body of the sleeve accessory 301 may range between 0.25 inches and 3.0 inches. In other embodiments, the sleeve accessory 301 may comprise a different natural shape than the shape of the bills 203 and 205, and may also have a non-uniform width or diameter ranging between 0.25 and 3.0 inches when in an un-stretched or unexpanded state.

The sleeve accessory 301 may be made of one or more compliant or partially compliant materials, such as latex, vinyl, natural and synthetic rubbers, silicone, nylon, polyethylene, polyurethane, polypropylene, and non-degradable or degradable elastomers. In preferred embodiments, the sleeve accessory 301 may be made of a polyisoprene (PI), a polyurethane (PU), a thermoplastic polyurethane (TPU), a styrene copolymer (SBS), and/or a thermoplastic elastomer (TPE). The material of the sleeve accessory 301 may range from completely transparent to translucent or frosty to opaque. Alternatively, the sleeve accessory 301 may include a finish that ranges from completely transparent to translucent or frosty to opaque. Different finishes may be used for different types of gynecological examinations or procedures. For example, a thicker and/or more opaque sleeve may be used for a surgical procedure, such as an electrosurgery procedure, while a thinner and/or more clear sleeve may be used for a gynecological examination or procedure.

The sleeve accessory 301 or a portion of the sleeve accessory 301 may optionally be coated with one or more bioactive or therapeutic agents, lubricants, or surface finishes. Examples of suitable bioactive or therapeutic agents include, but are not limited to, hormonal and non-hormonal contraceptive agents, cancer screening agents, vaginal spermicides, vaginal microbicides, antibacterial agents, antifungal agents, antiviral agents, anti-HIV agents, and cancer treatment agents, or combinations thereof. The bioactive or therapeutic agents may be in any suitable formulation that may be applied to the surface of a vaginal speculum, such as a liquid, gel and powder.

In some embodiments, lubricants may be applied to at least a portion of an inner surface of the sleeve accessory 301 and/or to an outer surface of the sleeve accessory 301. When applied to the inner surface of the sleeve accessory 301, the lubricant may, e.g., aid in positioning the sleeve accessory 301 on the insertion portion 211. When applied to an outer surface of the sleeve, the lubricant may, e.g., help the speculum 200 with the attached sleeve accessory 301 be more easily inserted into the patient. In other embodiments, the lubricant on the interior surface and/or exterior surface of the sleeve accessory 301 may instead be, or may be combined with, a powder applied to the sleeve accessory 301 or a surface texture finished into a material of the sleeve accessory 301. The powder and/or surface texture may likewise, e.g., aid the user in positioning the sleeve accessory 301 on the insertion portion 211, help the speculum 200 with the attached sleeve accessory 301 be more easily inserted into the patient, and so on. In various embodiments, the sleeve accessory 301 may come with lubricant and/or powder pre-applied, the sleeve accessory 301 may come in a kit with lubricant and/or powder included for the user to apply to the sleeve accessory 301, the sleeve accessory 301 may come with instructions that recommend types or brands of lubricants and/or powders for the user to apply to create the beneficial effects discussed above, etc.

As shown in FIG. 3, once positioned on the insertion portion 211, the sleeve accessory 301 surrounds the bills 203 and 205 and preferably has a snug fit around bill 203 and 205. As such, sleeve accessory 301 should not move along the bills 203 or 205 during insertion into the vagina or during a medical examination, procedure, or surgery being conducted on the vaginal or surrounding tissues. The sleeve accessory 301 may additionally include ribbed details 310 that help the sleeve accessory 301 remain securely fastened onto the insertion portion 211. In one embodiment, the ribbed details may be limited to a portion of the sleeve accessory 301 secured to the smaller, narrower, distal end of the insertion portion 211. In other embodiments, the ribbed details may, additionally or alternatively, be limited to a portion of the sleeve accessory 301 secured to the larger, proximal end of the insertion portion 211 near the handle 207, or be distributed throughout the length of the sleeve accessory 301. In some embodiments, the ribbed details may instead be, or may be combined with, texture differences or lubrication differences provided on an inner surface of the sleeve accessory 301 and/or gripping elements (e.g., such as flanges 505 shown in FIG. 4) positioned on an inner surface of the sleeve accessory 301 that may help the sleeve accessory 301 remain securely fastened onto the insertion portion 211.

The proximal opening of the sleeve accessory 301, as well as a distal opening included in some embodiments of the sleeve accessory 301, may have a ridged finish, shown as end ring 307. The ridged finish may be provided to give the user a ridge to aid the user in positioning the sleeve accessory 301 on the insertion portion 211, to finish the end of the sleeve accessory 301 so that the end of the sleeve accessory 301 is less easily ripped or otherwise damaged, to provide additional tension to adhere the sleeve accessory 301 to the insertion portion 211, and so on. The ridged finish may be provided as an end ring 307, which may be a rolled bead edge (i.e., similar to a condom) or may be formed from an encapsulated ring (i.e., a ring that is rolled into the end of the sleeve accessory 301 and cured). In other embodiments, the ridged finish may be provided as a dip in the material of the sleeve accessory 301, a secondary dip in another polymer material (e.g., of a different thickness, durometer, color, etc.) attached to the sleeve accessory 301, an otherwise attached or adhered secondary material that finishes the opening(s), and so on.

FIG. 4 illustrates another embodiment of a sleeve accessory for a medical speculum, shown as a sleeve accessory 501. The sleeve accessory 501 is designed similarly to sleeve accessory 301, with a cylindrical sleeve body configured to be slid over an insertion portion of a speculum, such as insertion portion 211 of speculum 200. The sleeve accessory 501 may have many of the same features as described above with respect to sleeve accessory 301, such as an end ring 507. The sleeve accessory 501 also includes flanges 505 to help the sleeve remain securely fastened onto the insertion portion 211. As shown in FIG. 4, similar to sleeve accessory 301, the cylindrical body of the sleeve accessory 501 has an open proximal end and an open distal end. However, in some embodiments, a sleeve accessory may instead have a closed distal end (e.g., the sleeve accessory 501 may wrap around the distal end of the bills 203 and 205 so as to enclose the top portion of the bills 203 and 205, or extend up to the distal end of the bills 203 and 205). In these embodiments, the sleeve accessory may further include a small hole or aperture (not shown) in the closed, distal end of the sleeve accessory, which may allow for visualization, tissue sampling, etc. through the otherwise closed distal end. Additionally, as shown in FIG. 4, the distal end of the sleeve accessory 501 nearly reaches the distal end of the bills 203 and 205. However, in other embodiments, a sleeve accessory may not reach the end of the bills 203 and 205 when the sleeve accessory is positioned on the bills 203 and 205 or may extend past the end of the bills 203 and 205.

FIG. 5 illustrates a sleeve accessory, shown as sleeve accessory 601, positioned on speculum 200. Sleeve accessory 601 is configured similarly to sleeves 301 and 501 discussed above, with a cylindrical sleeve body surrounding a lumen configured to receive an insertion portion of a speculum, such as insertion portion 211 of speculum 200, and open proximal and distal ends framed by end rings 607. As shown in FIG. 5, once positioned on the speculum 200, when a force is applied to the lever 209 and the bills 203 and 205 of the speculum 200 separate, the sleeve accessory 601 expands from a first state to a second state (i.e., from an unexpanded state to an expanded state). When the bills 203 and 205 separate, the sleeve accessory 601 may stretch to accommodate the increase in distance between bills 203 and 205. Beneficially, the expansion of the sleeve accessory 601 provides side wall retention for tissue encroachment from the side walls of the vagina, allowing the user to maintain an uninterrupted view of the vaginal cavity and cervix while viewing the vaginal cavity and cervix through the speculum 200. The expansion of the sleeve accessory 601 also works to prevent vaginal tissue or pubic hair from entering the opening between the bills 203 and 205, as the bills 203 and 205 may cause pinching of the tissue or pubic hair that is painful for the patient when the bills 203 and 205 are returned to the closed position at the conclusion of the procedure, examination, or surgery. Additionally, when the bills 203 and 205 are closed, the sleeve accessory 601 may return to its original state (e.g., the first state).

Figure 6B:
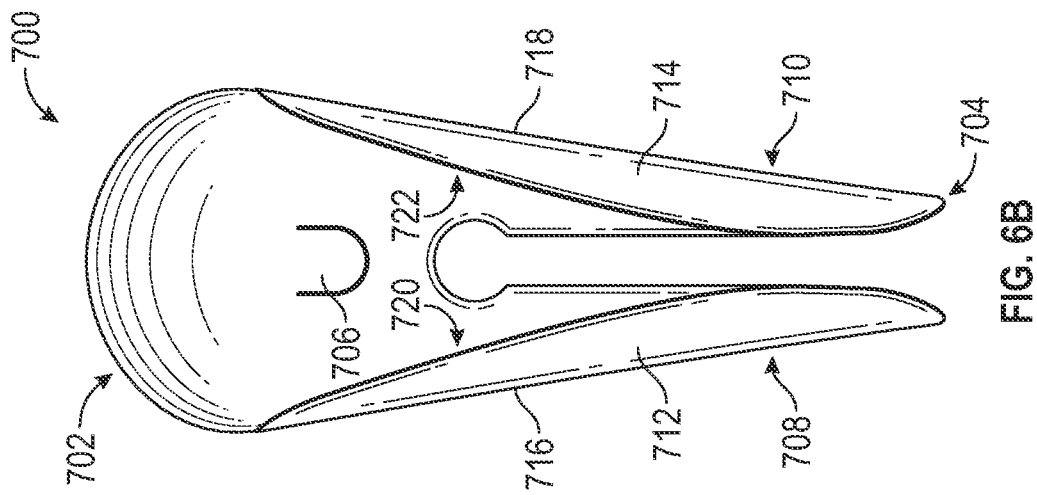
FIG. 6B is another bottom view of the applicator of FIG. 6A, in a folded position, according to an example embodiment.
Figure 6A:
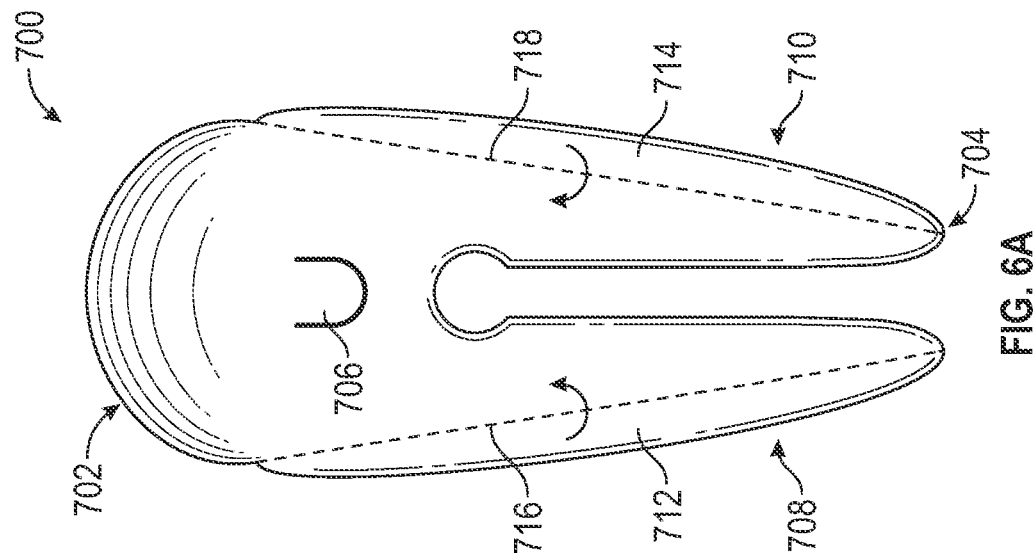
FIG. 6A is a bottom view of an applicator for a sleeve accessory, in an unfolded position, according to an example embodiment.

FIGS. 6A-6C illustrate an applicator 700 for a sleeve accessory (e.g., sleeve accessory 301, 501, and/or 601), according to one embodiment. The applicator 700 is used by a practitioner to facilitate the positioning of a sleeve accessory onto a medical speculum, such as speculum 200. A bottom view of the applicator 700 is shown in FIGS. 6A and 6B. As illustrated in FIG. 6A, according to one embodiment, the applicator 700 is flat and roughly oblong, with a broader proximal end 702 and a narrower distal end 704. The proximal end includes a tab 706 that may be pulled away from the main body of the applicator 700, while the distal end 704 splits into a first prong 708 and a second prong 710.

The applicator 700 further includes a first flap 712 and a second flap 714 formed into the sides of the applicator 700, where the first flap 712 is configured to fold at a first fold line 716 and the second flap 714 is configured to fold at a second fold line 718, as shown by the arrows of FIG. 6A. FIG. 6B illustrates the applicator 700 with the first flap 712 folded over the first fold line 716 and the second flap 714 folded over the second fold line 718. As shown in FIG. 6B, when the flaps 712 and 714 are folded over, the first flap 712 forms a first pocket 720 within the first prong 708 and the second flap 714 forms a second pocket 722 within the second prong 710.

The applicator 700 may be made of a stiff, noncompliant or minimally compliant material or of a flexible, more compliant material. Thus, the applicator 700 may be made of paper, cardboard, paperboard, or corrugated fiberboard. Alternatively, the applicator 700 may be made of natural or synthetic rubbers or of a plastic, such as latex, vinyl, silicone, polyethylene, polyurethane, polypropylene, polycarbonate, or non-degradable or degradable elastomers. In some embodiments, the applicator 700 may be designed for a single use and be disposable. In other embodiments, the applicator 700 may be designed to be reusable (e.g., designed to be sterilizable for reuse).

A top view of the applicator 700 positioned within a sleeve accessory, shown as sleeve accessory 801, is illustrated in FIG. 6C. The sleeve accessory 801 is designed similarly to sleeves 301, 401, 501, and 601, with a cylindrical sleeve body configured to be slid over an insertion portion of a speculum, such as insertion portion 211 of speculum 200. The sleeve accessory 801 further includes an open proximal end 802 framed by an end ring 807 and an open distal end 804. However, other embodiments of sleeve accessory 801 may include a closed distal end, one or more gripping elements (e.g., similar to ribbed details 310 or flanges 505), one or more coatings, one or more surface finishes, and so on, as described above with respect to sleeves 301, 501, and 601.

As illustrated in FIG. 6C, the applicator 700 is positioned within the sleeve accessory 801. In an exemplary embodiment, the applicator 700 and the sleeve accessory 801 are packaged together with the applicator 700 pre-inserted into the sleeve accessory 801 as shown in FIG. 6C. However, in other embodiments, a user may need to slide or otherwise position the applicator 700 into the sleeve accessory 801. In various embodiments, as shown, the applicator 700 is designed such that the oblong shape of the applicator 700, with the broader proximal end 702 narrowing to the distal end 704, fits the shape of the sleeve accessory 801, which may also narrow from the broader proximal end 802 to the narrower distal end 804. Accordingly, the applicator 700 may be easily positioned within the sleeve accessory 801 until the prongs 708 and 710 abut the walls of the sleeve accessory 801. In some embodiments, the prongs 708 and 710 may create friction between the applicator 700 and walls of the sleeve accessory 801 such that there is at least some resistance to the applicator 700 being slid out from the sleeve accessory 801. Additionally, the tab 706 is configured to be tucked over the top edge (e.g., over the end ring 807) of the proximal end 802 of the sleeve accessory 801 once the applicator 700 has been slid into the sleeve accessory 801. Thus, the tab 706 and/or the resistance created by friction between the prongs 708 and 710 and the walls of the sleeve accessory 801 may prevent the applicator 700 from inadvertently sliding out of the sleeve accessory 801. Instead, once the applicator 700 is inserted into the sleeve accessory 801, at least a small force may need to be applied to remove the applicator 700 from the sleeve accessory 801.

Additionally, the prongs 708 and 710 are configured such that when the applicator 700 is inserted into the sleeve accessory 801, the prongs 708 and 710 hold the interior of the sleeve accessory 801 at least partially open. In this way, the prongs 708 and 710 allow a user to easily slide an insertion portion of a medical speculum into the interior of sleeve accessory 801. Furthermore, the prongs 708 and 710 are spaced apart such that the space between the first fold line 716 and the second fold line 718 are at least as wide as the insertion portion of the medical speculum. As such, the insertion portion may be slid in between the prongs 708 and 710 and through the pockets 720 and 722 formed in the prongs 708 and 710. Thus, the prongs 708 and 710 of the applicator 700 may guide the insertion portion of the medical speculum into the lumen of sleeve accessory 801.

As shown in FIG. 6C, in some embodiments, the distal ends 704 of the prongs 708 and 710 may not reach the distal end 804 of the sleeve accessory 801. However, in other embodiments, the applicator 700 may be configured such that the ends of the prongs 708 and 710 meet the distal end 804 of the sleeve accessory 801, or the applicator 700 may be configured such that the ends of the prongs 708 and 710 extend past the distal end 804 of the sleeve accessory 801.

FIGS. 7A-7G illustrate an applicator 900 for a sleeve accessory (e.g., sleeve accessory 301, 501, 601, 801, and/or 1001). The applicator 900 may include the same or similar components and/or properties as the applicator 801. The applicator 900 is used by a practitioner to facilitate the positioning of a sleeve accessory onto a medical speculum, such as speculum 200.

Figure 7A:
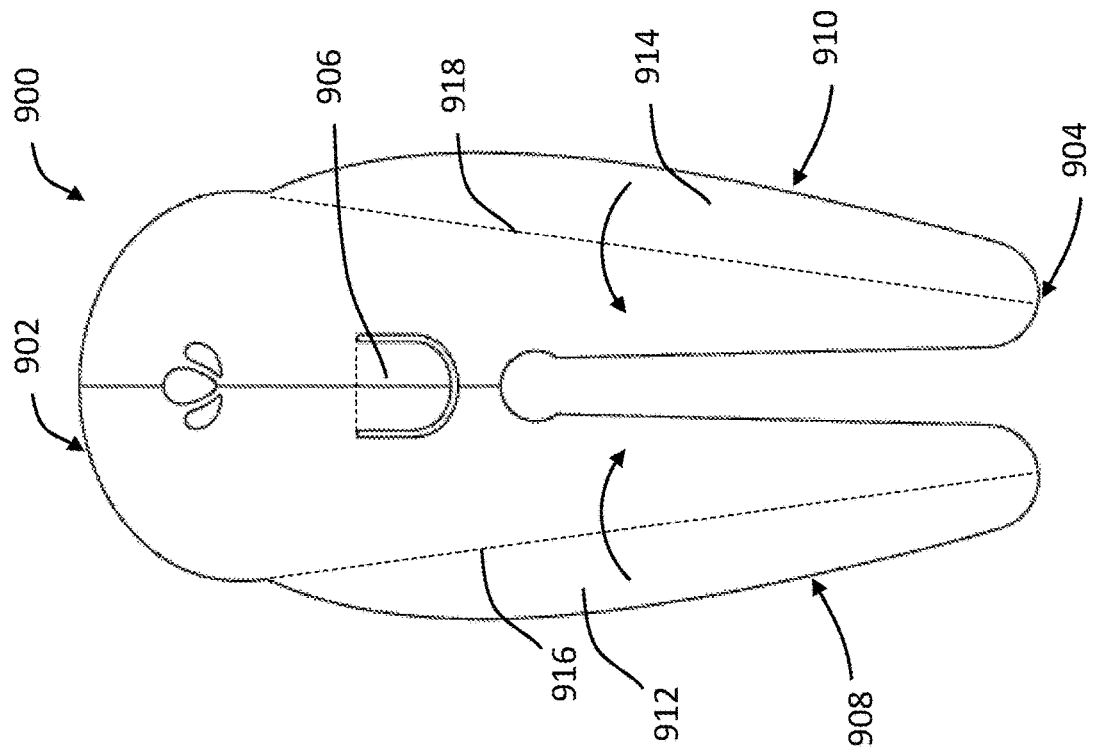
FIG. 7A is a bottom perspective view of an applicator for a sleeve accessory, in an unfolded position, according to an example embodiment.
Figure 7B:
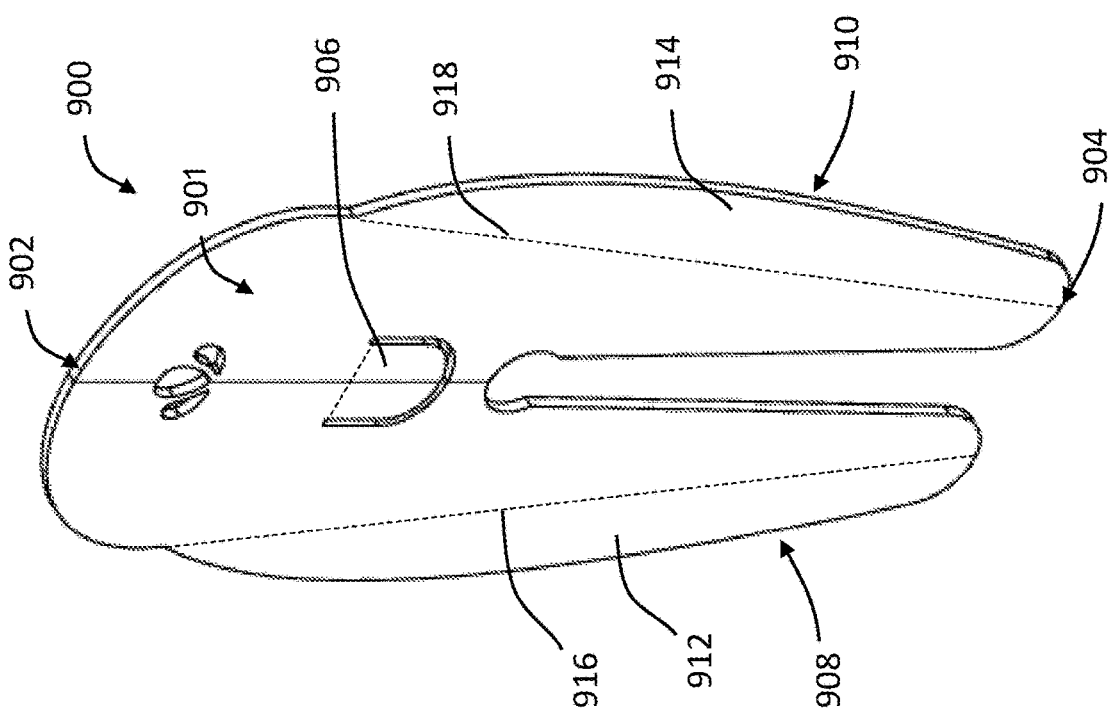
FIG. 7B is a bottom view of the applicator of FIG. 7A, in an unfolded position, according to an example embodiment.
Figure 7D:
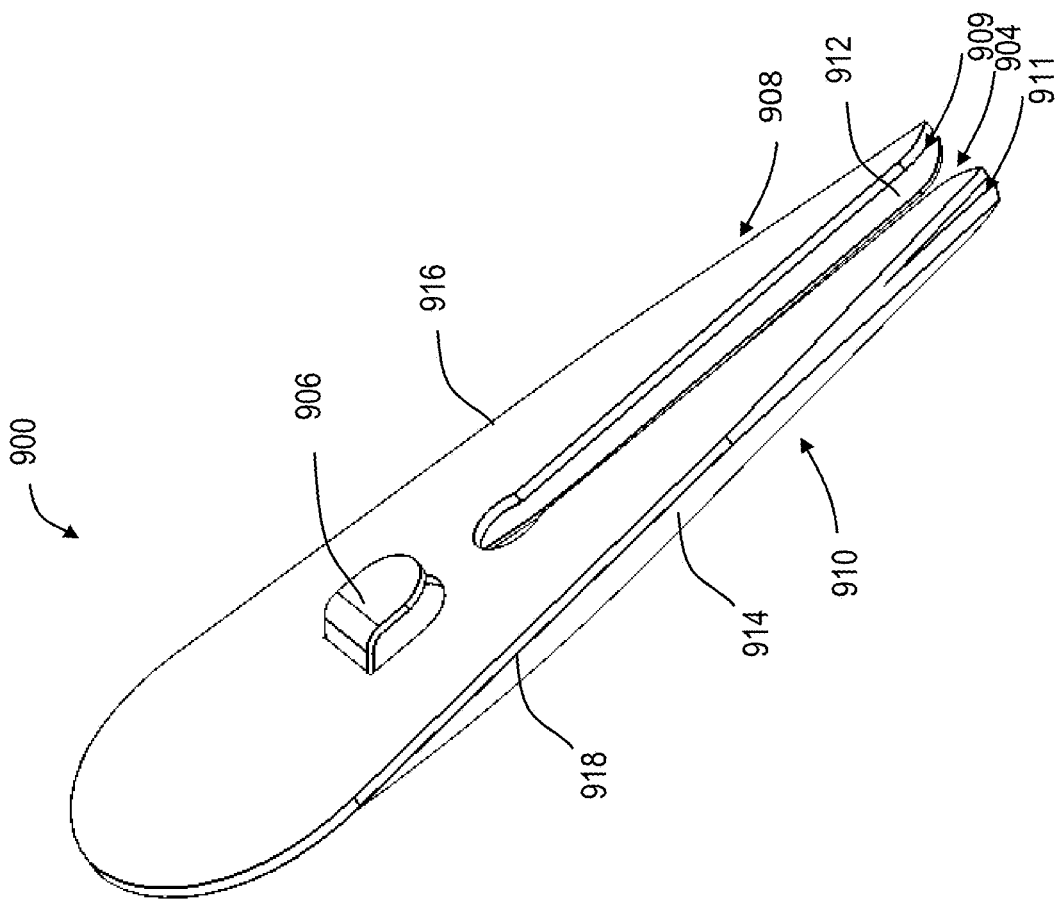
FIG. 7D is a top perspective view of the applicator of FIG. 7A, in a folded position, according to an example embodiment.
Figure 7C:
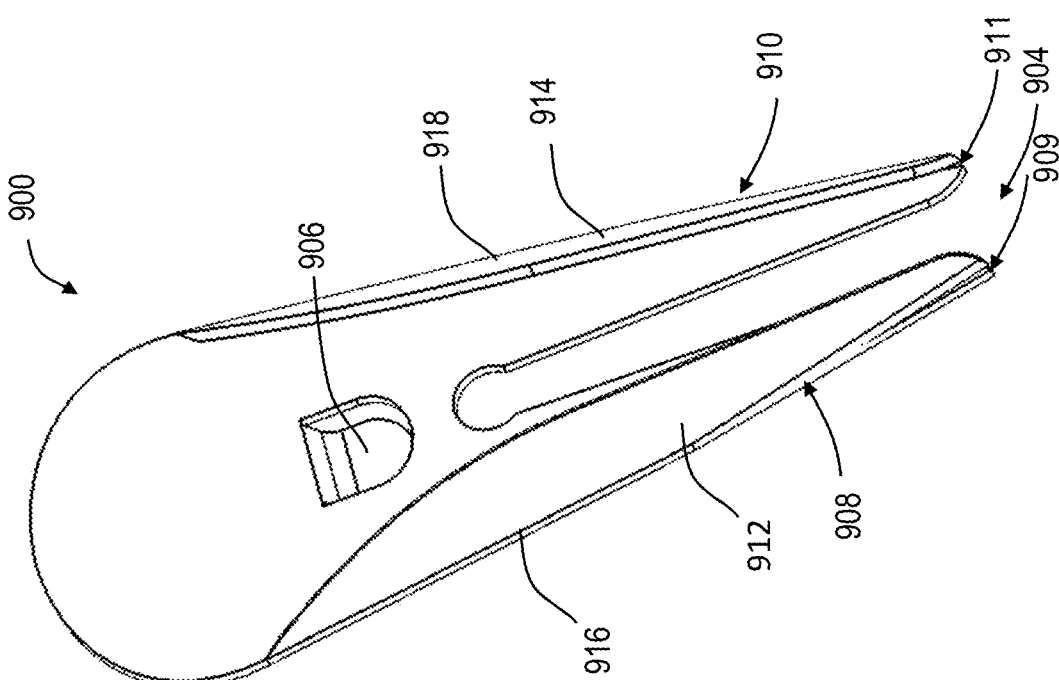
FIG. 7C is a bottom perspective view of the applicator of FIG. 7A, in a folded position, according to an example embodiment.
Figure 7G:
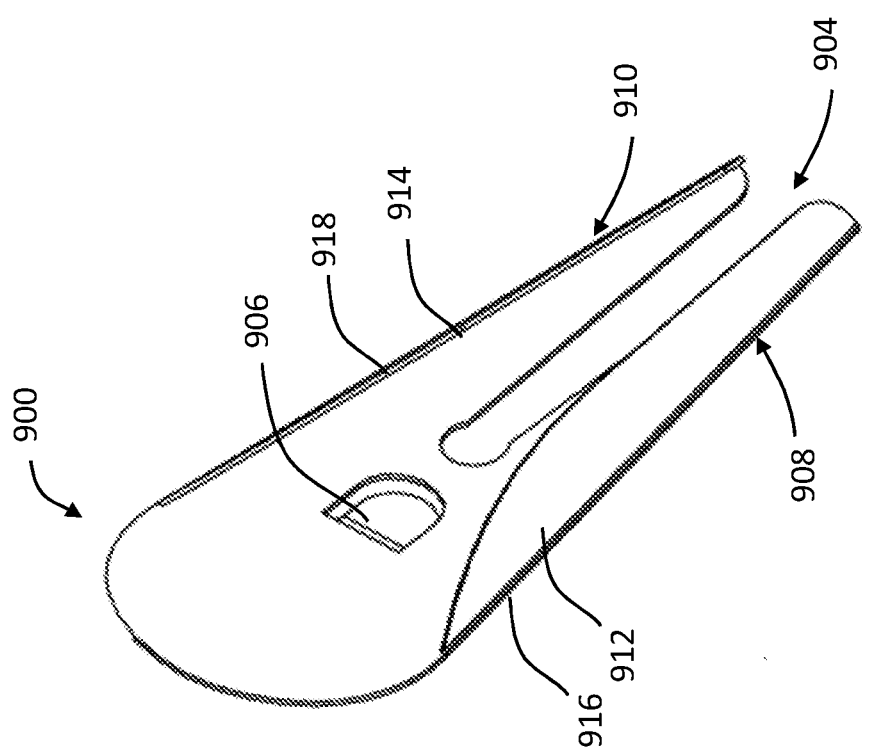
FIG. 7G is a bottom perspective view of an example of an applicator, in a folded position, according to an example embodiment.

FIGS. 7A and 7B illustrate the applicator 900 in an unfolded position. As illustrated in FIGS. 7A and 7B, the applicator 900 in the unfolded position is generally flat and roughly oblong. For example, the applicator 900 includes a broader proximal end portion 902 and a narrower distal end portion 904. The proximal end portion 902 includes a tab 906 that may be pulled away from a main body 903 of the applicator 900. As described in more detail below, the distal end portion 904 splits into a first prong 908 and a second prong 910.

The applicator 900 further includes a first flap 912 and a second flap 914 formed into sides of the applicator 900. As shown in FIGS. 7A and 7B, when the applicator 900 is in the unfolded position, the first and second flaps 912, 914 may extend outwardly from the proximal end portion 902 of the applicator 900. The first flap 912 is configured to fold along a first fold line 916 and the second flap 914 is configured to fold along a second fold line 918, in the direction shown by the arrows of FIG. 7B. Folding the first and second flaps 912, 914 allows the applicator 900 to have a reduced profile for insertion into the sleeve accessory. Folding the first and second flaps 912, 914 may desirably allow the applicator 900 to be shaped to conform with an interior volume and/or surface of the corresponding sleeve accessory.

The applicator 900 may be made of a stiff, noncompliant or minimally compliant material or of a flexible, more compliant material. In some embodiments, the applicator 900 may be made of paper, cardboard, paperboard, or corrugated fiberboard. In some embodiments, the applicator 900 may be made of natural or synthetic rubbers or of a plastic, such as latex, vinyl, silicone, polyethylene, polyurethane, polypropylene, polycarbonate, and/or non-degradable or degradable elastomers. In some embodiments, the applicator 900 may be designed for a single use and be disposable. In other embodiments, the applicator 900 may be designed to be reusable (e.g., be designed to be sterilizable for reuse).

FIGS. 7C-7G illustrate the application 900 in a folded configuration. For example, FIGS. 7C-7G illustrate the applicator 900 with the first flap 912 folded over the first fold line 916 and the second flap 914 folded over the second fold line 918. In some embodiments, the applicator 900 folds entirely along the fold lines 916, 918 (see FIG. 7G). As shown, when the flaps 912 and 914 are folded over, the first flap 912 forms a first pocket 920 within the first prong 908 and the second flap 914 forms a second pocket 922 within the second prong 910. In addition, in the folded configuration, the tab 906 may be pulled away from a main body 903 of the applicator 900. Pulling the tab 906 away from the main body 903 of the applicator 900 forms a receiving space between the tab 906 and the main body 903 that is configured to receive at least a portion of the sleeve accessory to secure and/or otherwise retain the sleeve accessory to the applicator 900. The tab 906 receiving space formed between the tab 906 and the main body 903 may be sized to secure an end of a sleeve accessory, such as the sleeve accessory 1001, when the sleeve accessory is being applied to the speculum. The tab 906 may be defined by a securement mechanism. The securement mechanism (e.g., the tab) may secure the sleeve accessory such that an external device, such as a person's hand, tissue, etc. may not be needed to apply the sleeve accessory to the medical speculum. In some embodiments, when the sleeve accessory has been appropriately positioned on the speculum, the tab releases the sleeve accessory and is pulsed away from the sleeve accessory, as described in more detail below.

Figure 8B:
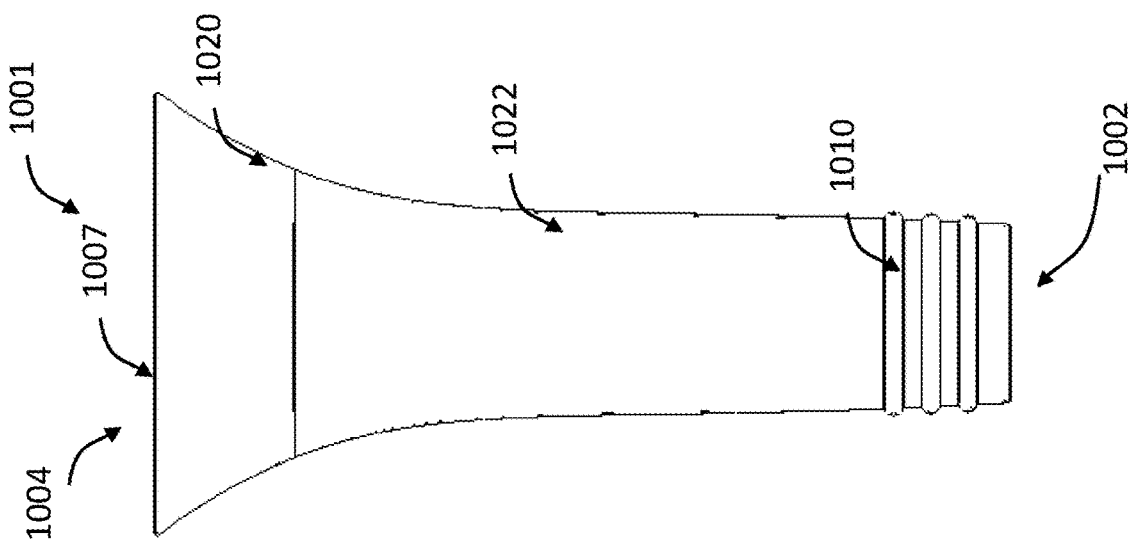
FIG. 8B is a top view of the sleeve accessory of FIG. 8A, in an uncompressed position, according to an example embodiment.
Figure 8A:
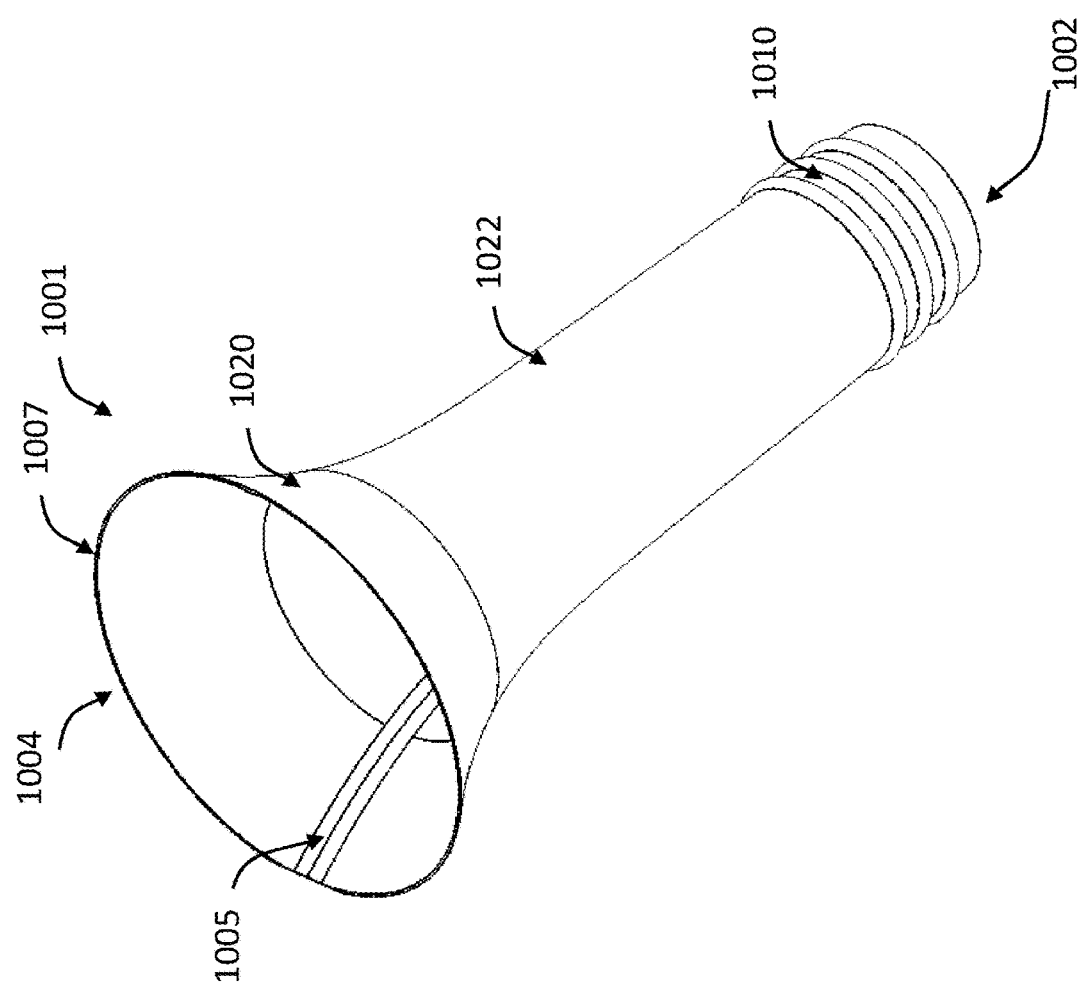
FIG. 8A is a top perspective view of a sleeve accessory for a medical speculum, in an uncompressed position, according to an example embodiment.
Figure 8D:
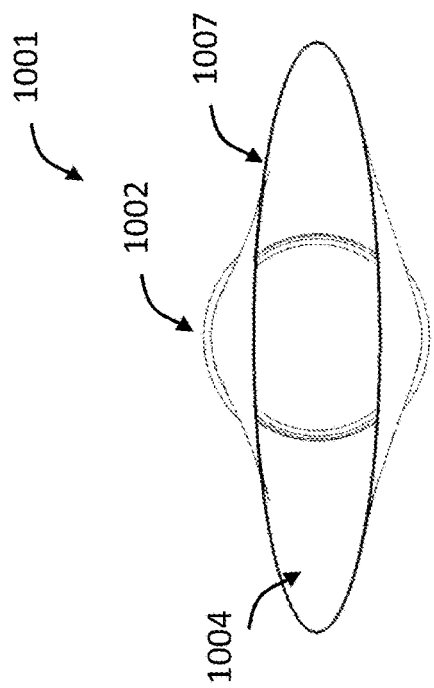
FIG. 8D is a rear view of the sleeve accessory of FIG. 8A, in a compressed position, according to an example embodiment.
Figure 8C:
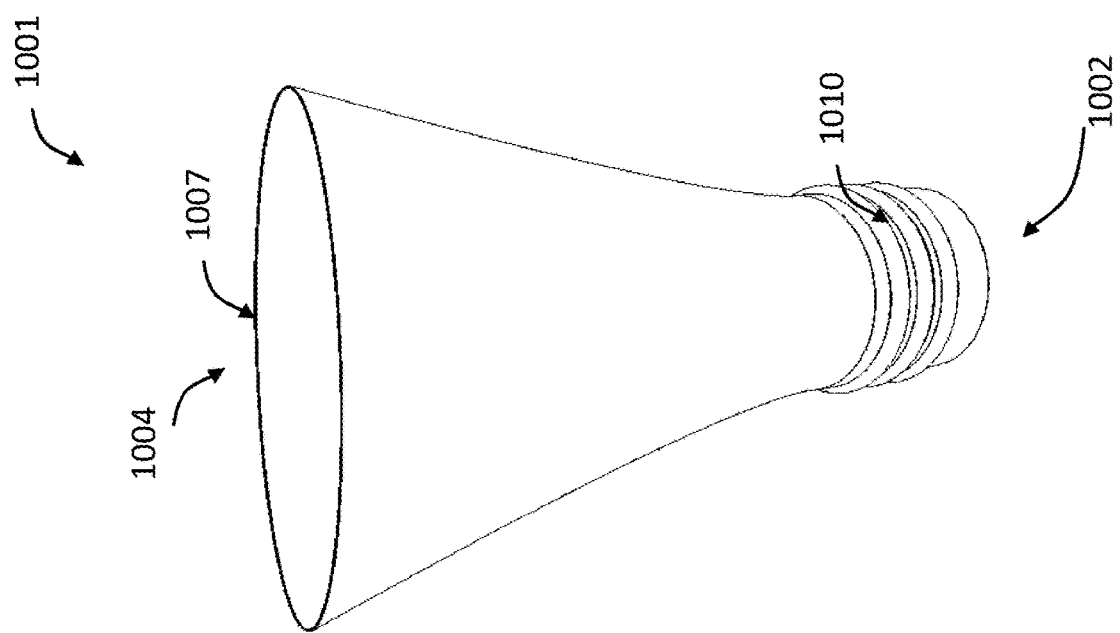
FIG. 8C is a top perspective view of the sleeve accessory of FIG. 8A, in a compressed position, according to an example embodiment.
Figure 8F:
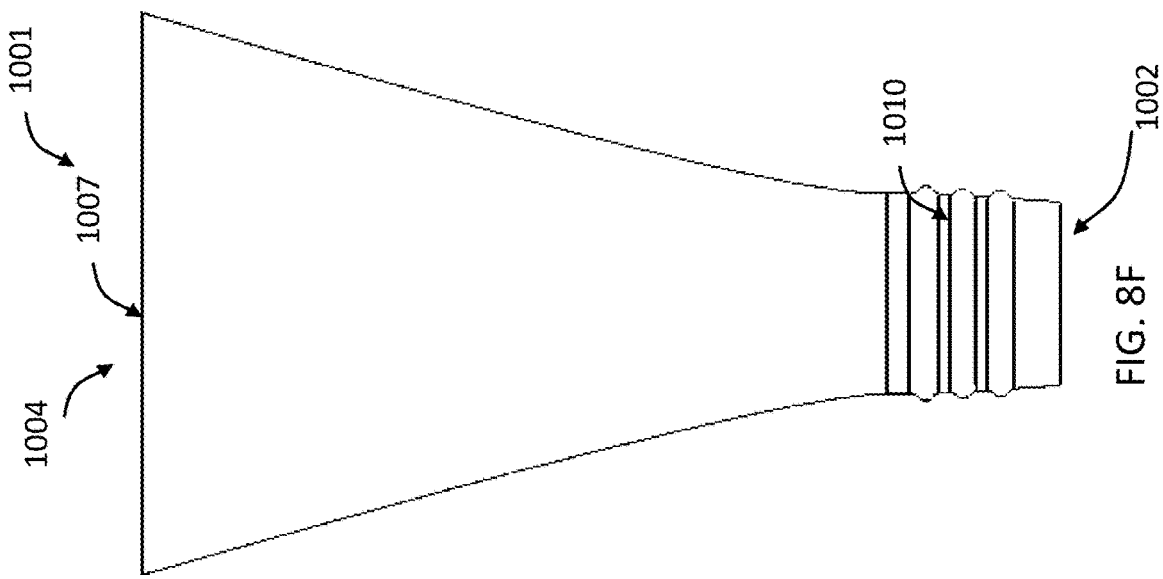
FIG. 8F is a top view of the sleeve accessory of FIG. 8A, in a compressed position, according to an example embodiment.
Figure 8E:
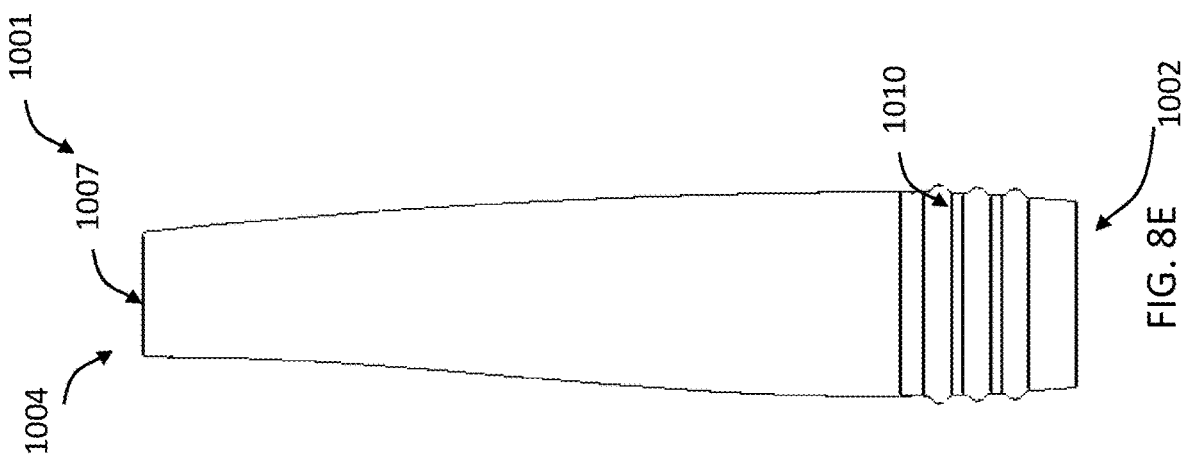
FIG. 8E is a side view of the sleeve accessory of FIG. 8A, in a compressed position, according to an example embodiment.
Figure 8H:
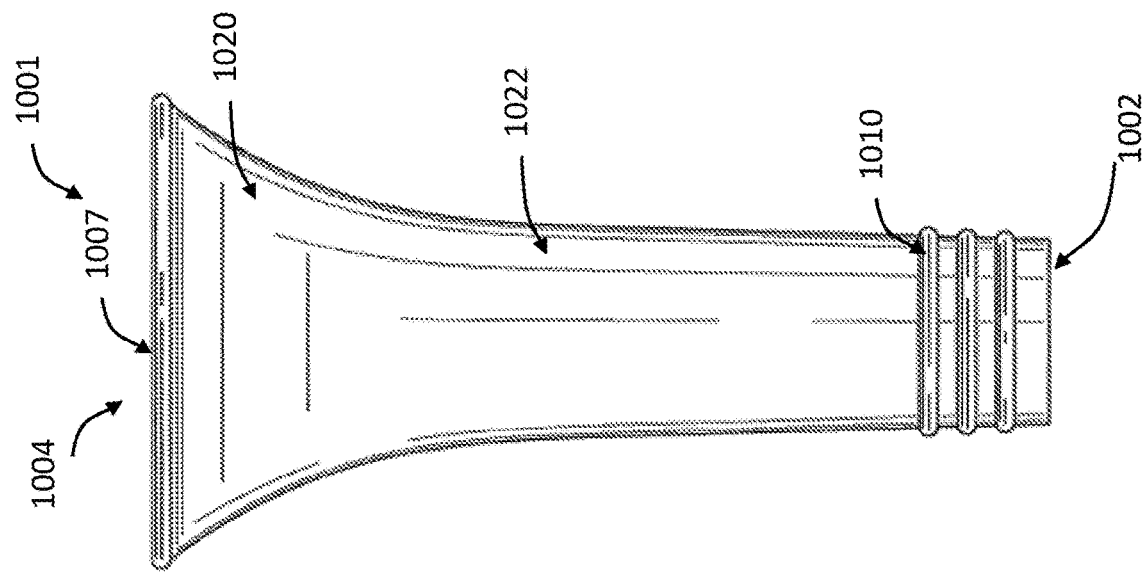
FIG. 8H is a top view of the variation of the sleeve accessory of FIG. 8G, in an uncompressed position, according to an example embodiment.
Figure 8G:
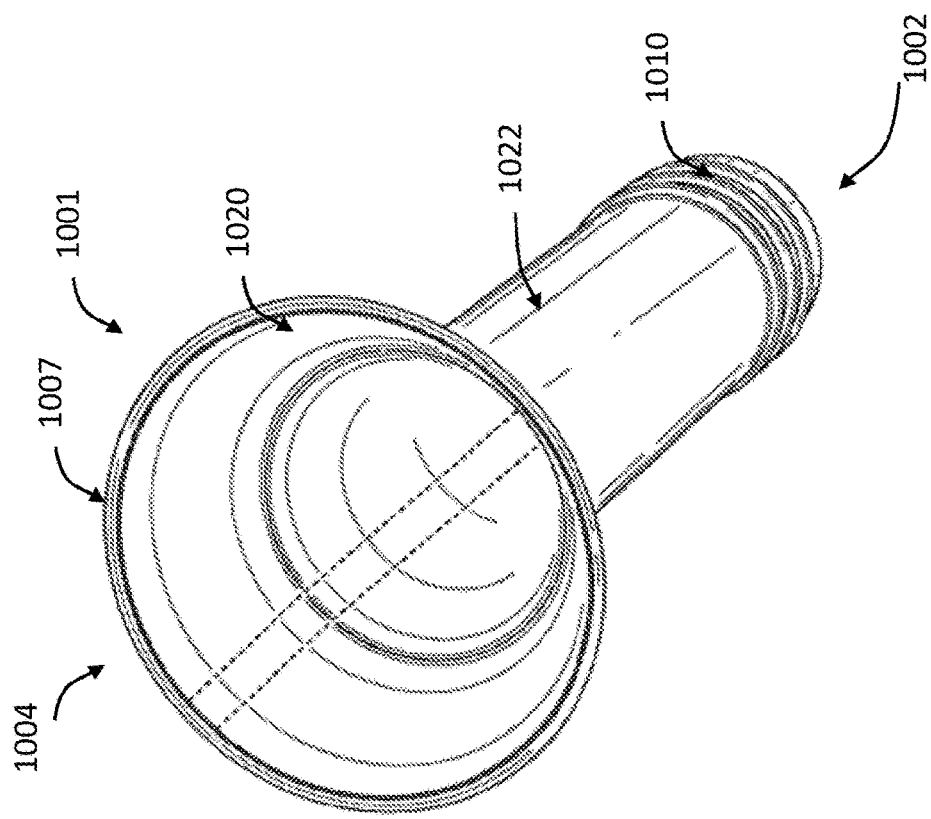
FIG. 8G is a top perspective view of a variation of the sleeve accessory of FIG. 8A, in an uncompressed position, according to an example embodiment.
Figure 8J:
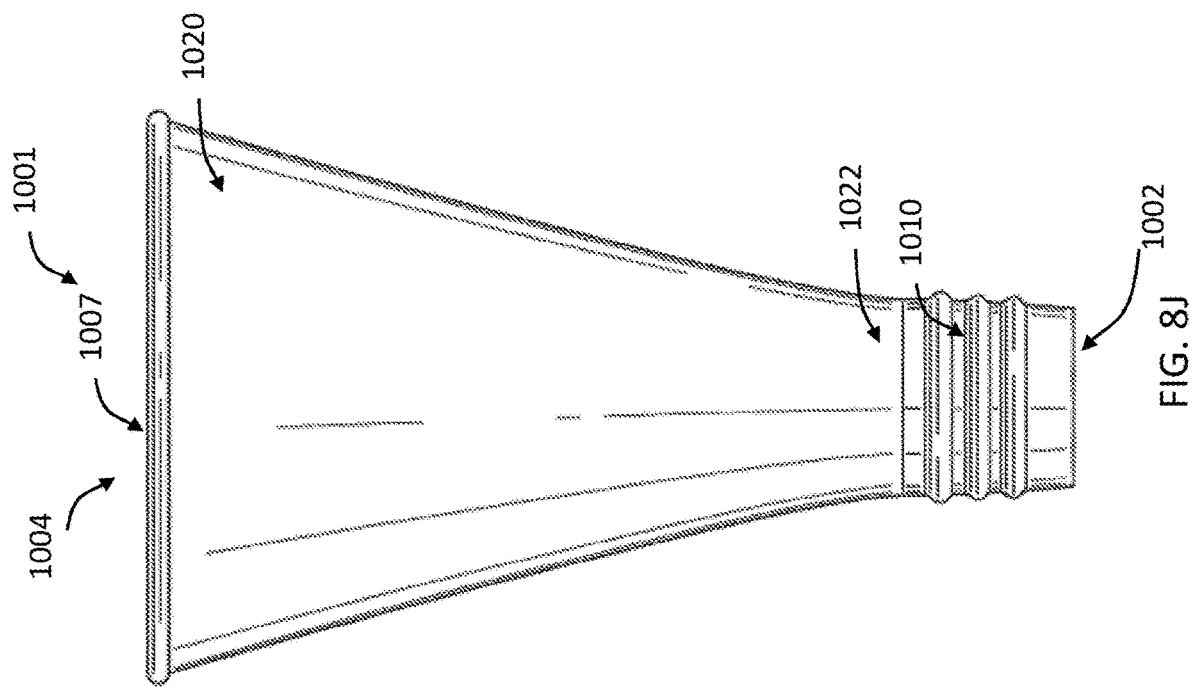
FIG. 8J is a top view of the sleeve accessory of FIG. 8G, in a compressed position, according to an example embodiment.
Figure 8I:
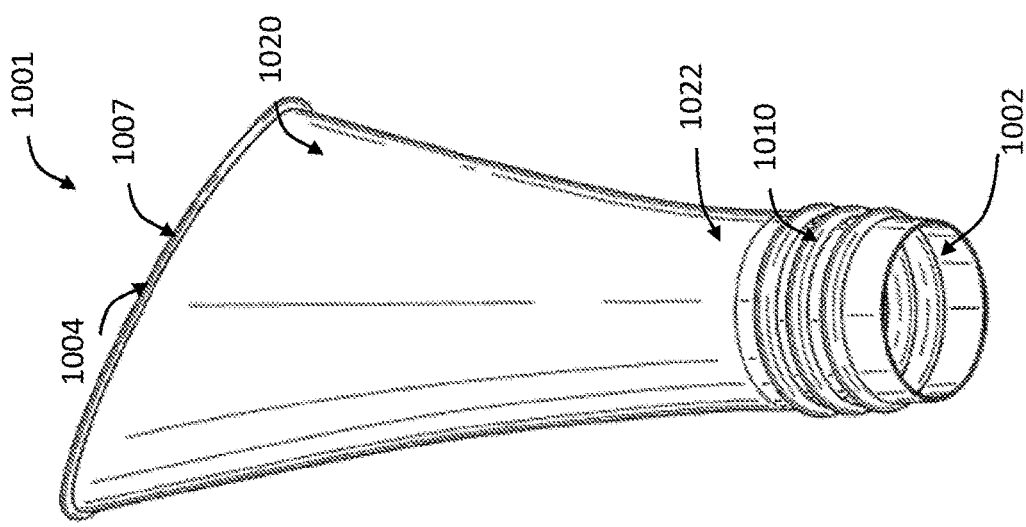
FIG. 8I is a top perspective view of the sleeve accessory of FIG. 8G, in a compressed position, according to an example embodiment.
Figure 8L:
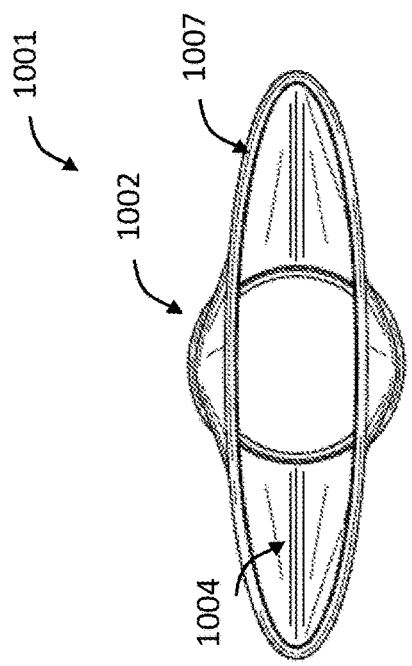
FIG. 8L is a rear view of the sleeve accessory of FIG. 8G, in a compressed position, according to an example embodiment.
Figure 8K:
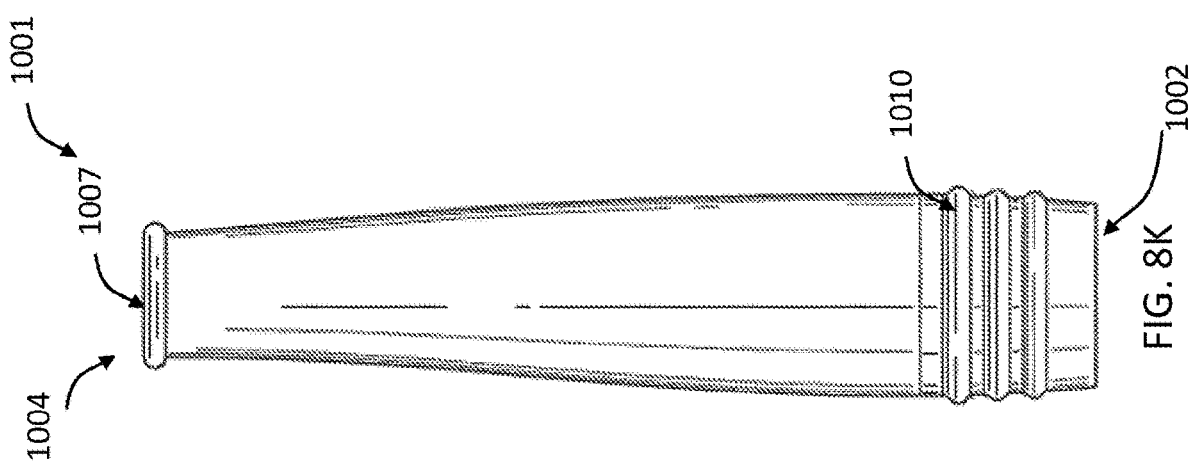
FIG. 8K is a side view of the sleeve accessory of FIG. 8G, in a compressed position, according to an example embodiment.
Figure 8N:
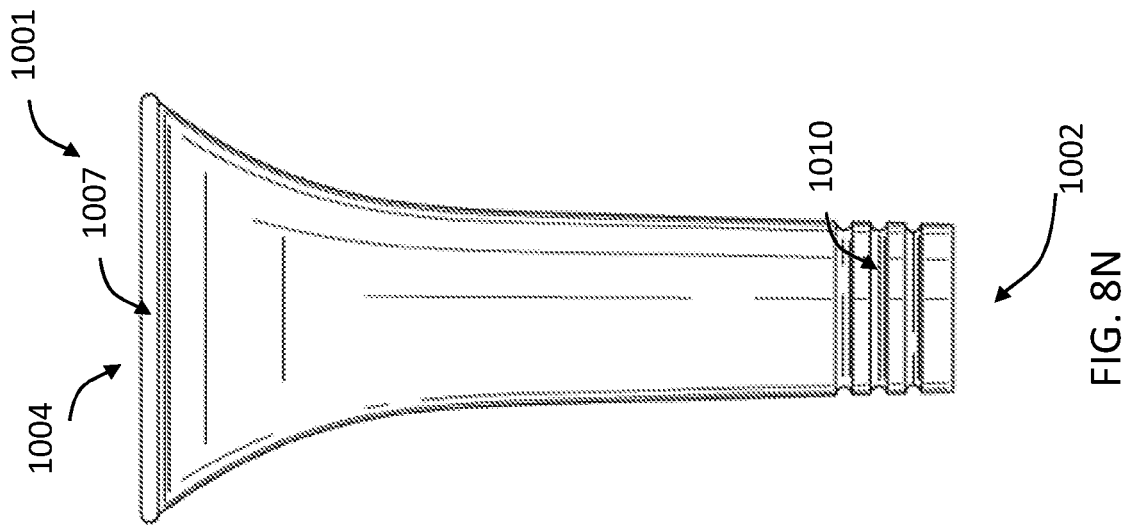
FIG. 8N is a top view of the variation of the sleeve accessory of FIG. 8M, in an uncompressed position, according to an example embodiment.
Figure 8M:
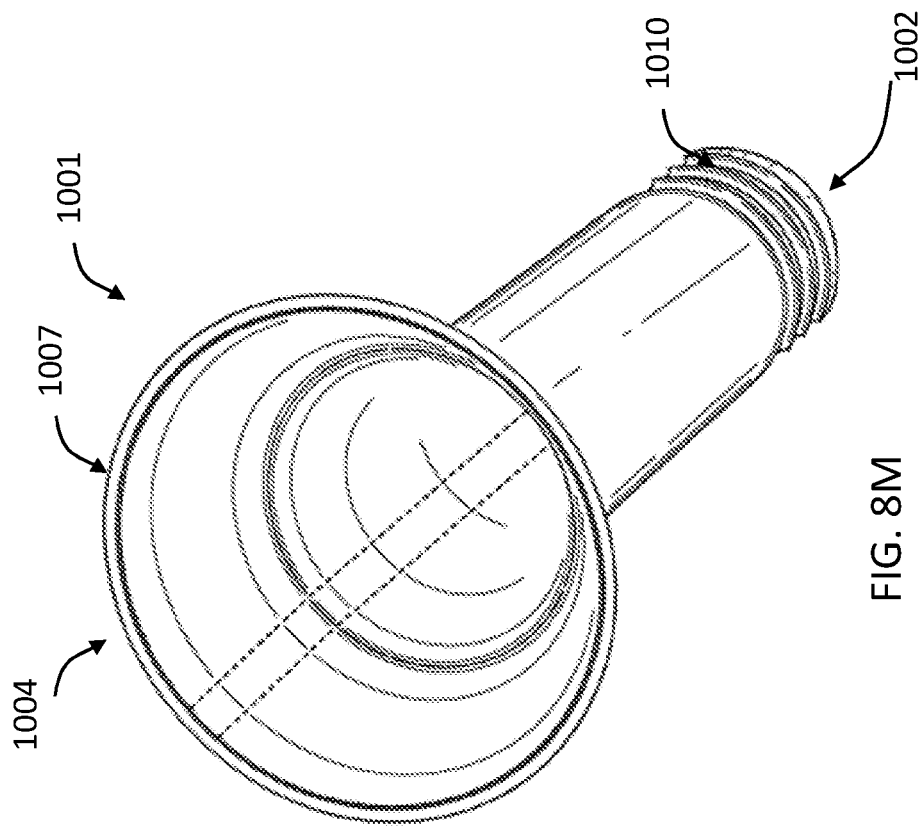
FIG. 8M is a top perspective view of a variation of the sleeve accessory of FIG. 8A, in an uncompressed position, according to an example embodiment.
Figure 8P:
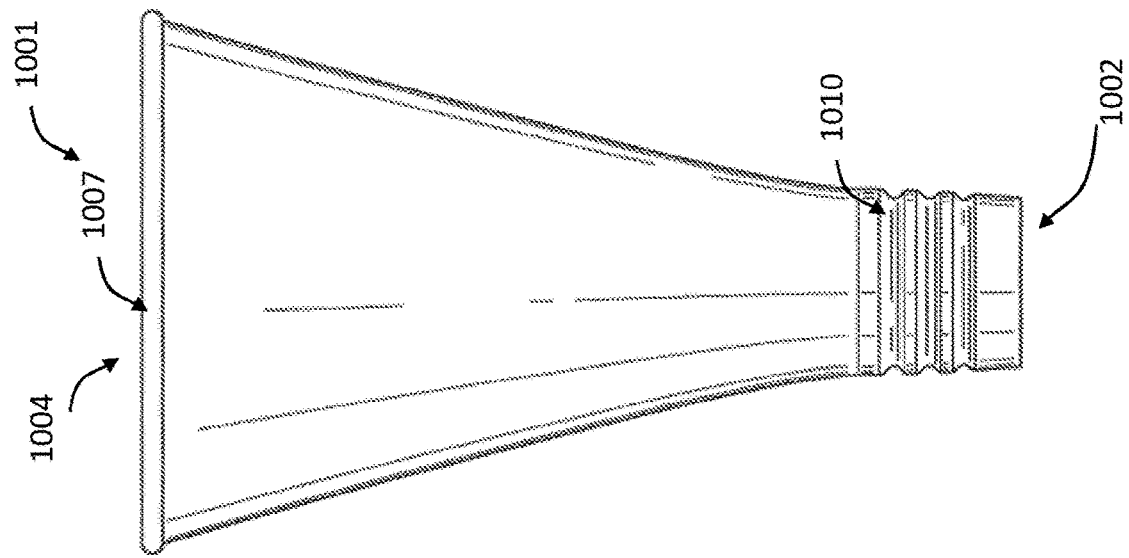
FIG. 8P is a top view of the sleeve accessory of FIG. 8M, in a compressed position, according to an example embodiment.
Figure 8O:
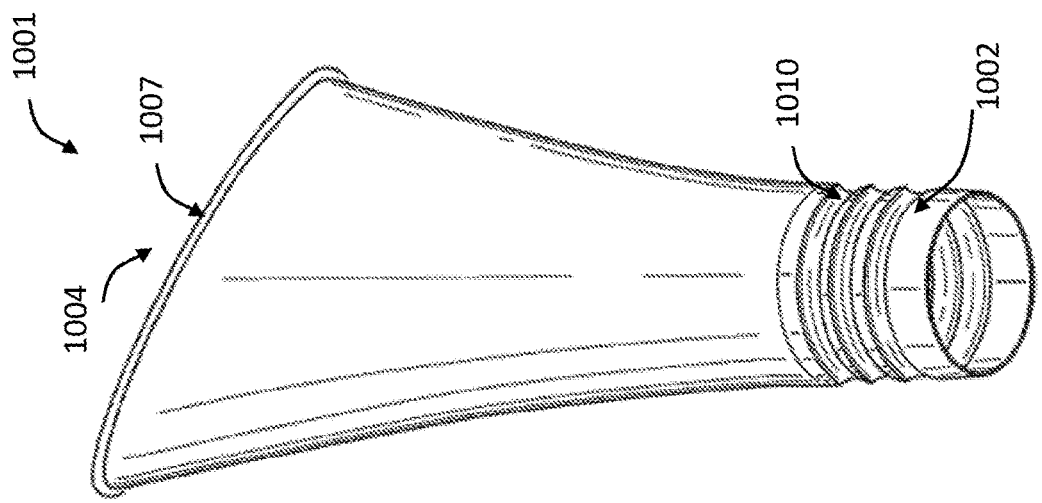
FIG. 8O is a top perspective view of the sleeve accessory of FIG. 8M, in a compressed position, according to an example embodiment.
Figure 8R:
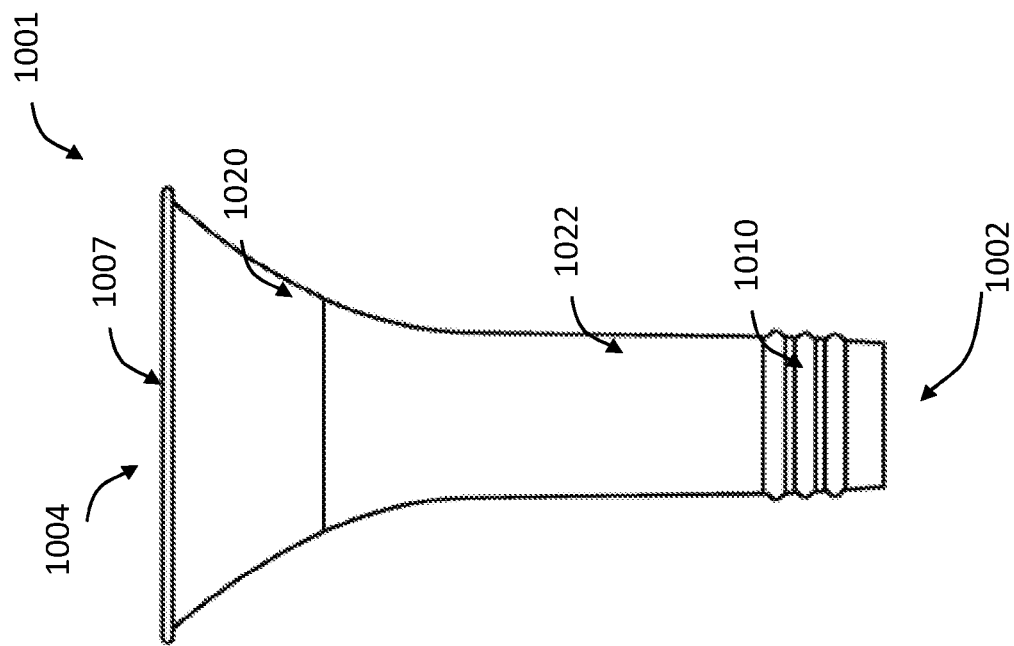
FIG. 8R is a top view of the sleeve accessory of FIG. 8Q, in an uncompressed position, according to an example embodiment.
Figure 8Q:
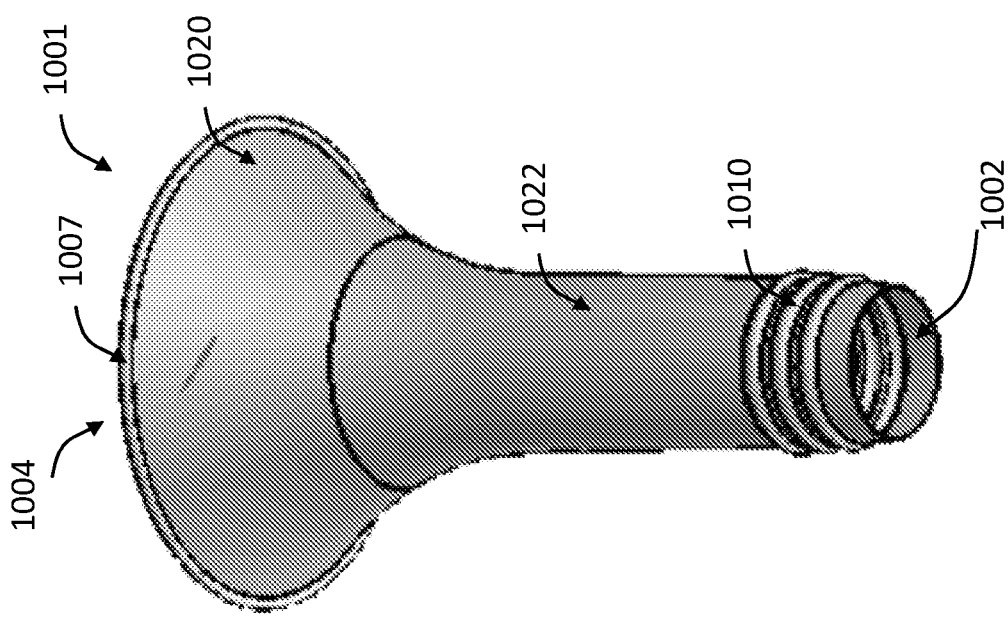
FIG. 8Q is a top perspective view of a sleeve accessory, in an uncompressed position, according to an example embodiment.
Figure 9C:
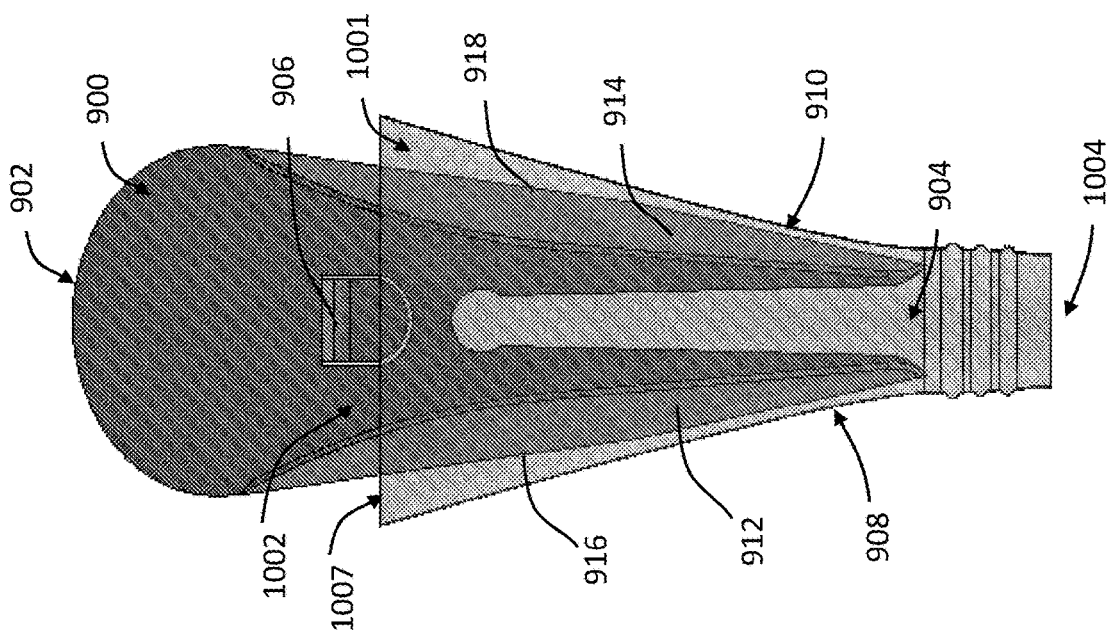
FIG. 9C is a top view of the applicator of FIGS. 7A-7F at least partially in the sleeve accessory of FIGS. 8A-8F, according to an example embodiment.
Figure 9D:
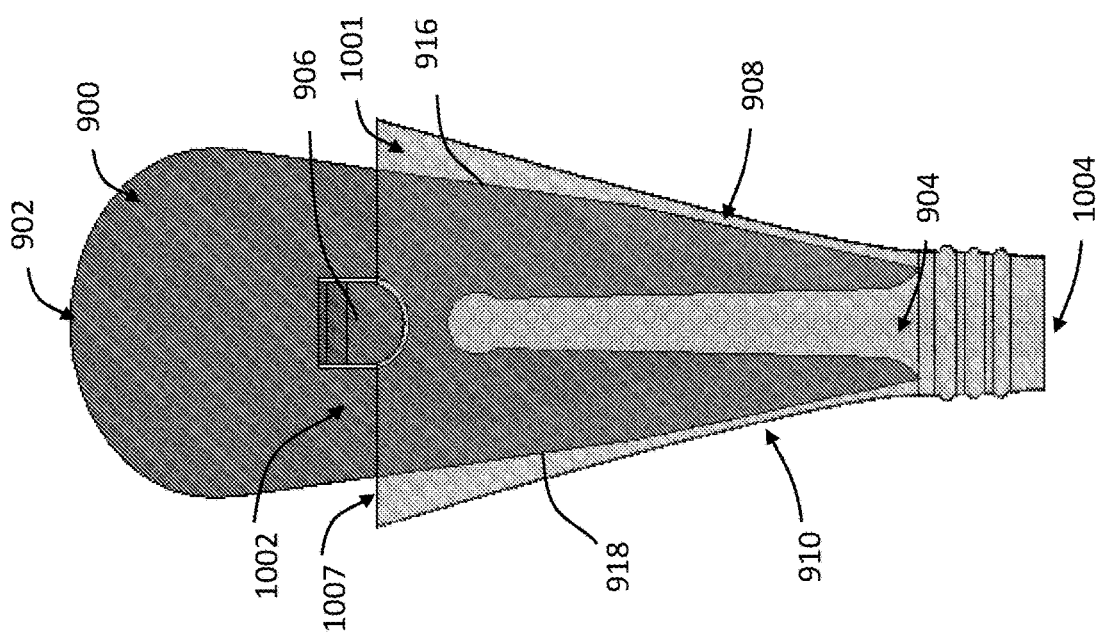
FIG. 9D is a bottom view of the applicator of FIGS. 7A-7F at least partially in the sleeve accessory of FIGS. 8A-8F, according to an example embodiment.
Figure 9F:
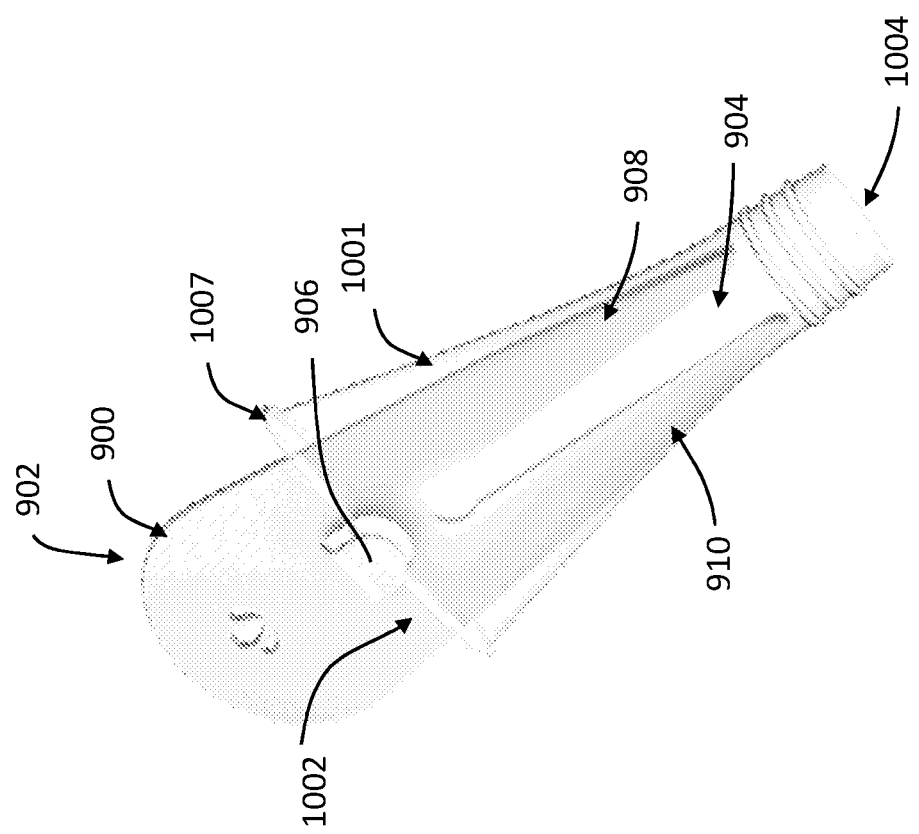
FIG. 9F is a bottom perspective view of an applicator at least partially in a sleeve accessory, according to an example embodiment.
Figure 9E:
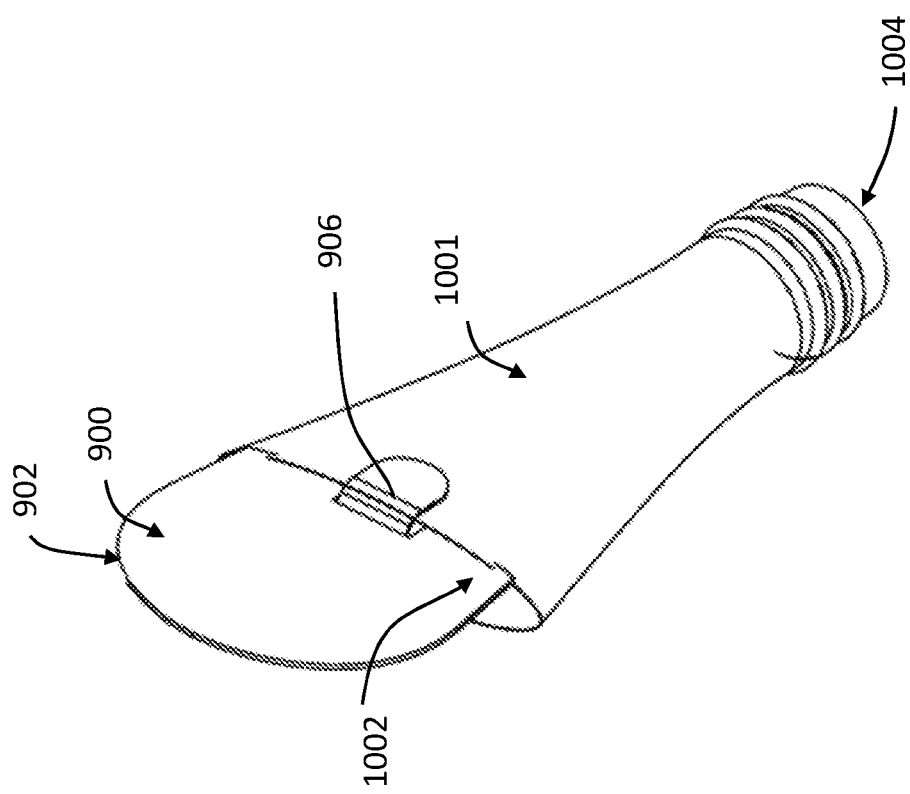
FIG. 9E is a bottom perspective view of an applicator at least partially in a sleeve accessory, according to an example embodiment.

FIGS. 8A-8Q illustrate an example of a sleeve accessory 1001, which may be designed similarly to and/or include the same or similar materials, properties and/or advantages of the sleeve accessories 301, 401, 501, 601, 801. For example, the sleeve accessory 1001 may define a cylindrical sleeve body configured to be slid over an insertion portion of a speculum, such as insertion portion 211 of speculum 200. The sleeve accessory 100 may be molded from a single or various materials, such as via blow-molding.

The sleeve accessory 1001 includes an open proximal end 1002 and an open distal end 1004. In some embodiments, the proximal end 1002 is framed by an end ring or rib 1007. For example, FIGS. 8G-8Q illustrate examples of the sleeve accessory 1001 in which the proximal end 1002 includes a rib 1007. As shown, the rib may extend about all or a portion of the proximal end 1002 of the sleeve accessory 1001. In some embodiments, the rib 1007 extends in a proximal direction from the proximal end 1002 of the sleeve accessory such that the rib 1007 is positioned at least partially over or adjacent to the proximal end 1002 and about a circumference of the proximal end 1002 of the sleeve accessory 1001. In some embodiments, the rib 1007 may extend around an outer surface of the sleeve accessory 1001 at least partially over or adjacent to the proximal end 1002. The rib 1007 may include a convex shape (shown in FIGS. 8G-8Q) or concave shape (not shown, but may include a similar shape and configuration to at least one of the ribbed details 1010 shown in FIGS. 8M-8P).

In some embodiments (not shown), the sleeve accessory 1001 may include a closed distal end, one or more gripping elements (e.g., similar to ribbed details 310 or flanges 505), one or more coatings, one or more surface finishes, and so on, as described above with respect to sleeve accessories 301, 501, 601, 801. In some embodiments, the sleeve accessories include a coating, such as a cornstarch coating or other lubricant. The coating may beneficially help to reduce tackiness of the material of the sleeve accessory and encourage easier application of the sleeve accessory to the speculum 200. For example, the sleeve accessories 301, 501, 601, 801, 1001 or a portion of each sleeve accessory may optionally be coated with one or more bioactive or therapeutic agents, lubricants, or surface finishes. Examples of suitable bioactive or therapeutic agents include, but are not limited to, hormonal and non-hormonal contraceptive agents, cancer screening agents, vaginal spermicides, vaginal microbicides, antibacterial agents, antifungal agents, antiviral agents, anti-HIV agents, and cancer treatment agents, or combinations thereof. The bioactive or therapeutic agents may be in any suitable formulation that may be applied to the surface of a vaginal speculum, such as a liquid, gel and powder.

In some embodiments, lubricants may be applied to at least a portion of an inner surface of each sleeve accessory and/or to an outer surface of each sleeve accessory. When applied to the inner surface of the sleeve accessory, the lubricant may, e.g., aid in positioning the sleeve accessory on the insertion portion 211. When applied to an outer surface of the sleeve, the lubricant may, e.g., help the speculum 200 with the attached sleeve accessory 301 be more easily inserted into the patient. The lubricant may beneficially help to reduce tackiness of the material of the sleeve accessory and encourage easier application of the sleeve accessory to the speculum 200. In other embodiments, the lubricant on the interior surface and/or exterior surface of the sleeve accessory may instead be, or may be combined with, a powder applied to the sleeve accessory or a surface texture finished into a material of the sleeve accessory. The powder and/or surface texture may likewise, e.g., aid the user in positioning the sleeve accessory on the insertion portion 211, help the speculum 200 with the attached sleeve accessory be more easily inserted into the patient, and so on. In various embodiments, the sleeve accessory may come with lubricant and/or powder pre-applied, the sleeve accessory may come in a kit with lubricant and/or powder included for the user to apply to the sleeve accessory, the sleeve accessory may come with instructions that recommend types or brands of lubricants and/or powders for the user to apply to create the beneficial effects discussed above, etc.

As shown in FIGS. 8A-8P, the sleeve accessory includes include ribbed details 1010 that help the sleeve accessory 1001 remain securely fastened onto the insertion portion 211 and/or the applicator 900. In some embodiments, the ribbed details 1010 may be limited to a portion of the sleeve accessory 1001 secured to the smaller, narrower, distal end of the insertion portion 211. In some embodiments, the ribbed details may, additionally or alternatively, be limited to a portion of the sleeve accessory 301 secured to the larger, proximal end of the insertion portion 211 near the handle 207, or be distributed throughout the length of the sleeve accessory 301.

The ribbed details 1010 may include three ribbed details. In some embodiments, the ribbed details 1010 may include one, two, three, four or more ribbed details 1010. In some embodiments, the ribbed details 1010 extend about an exterior surface of the sleeve accessory 1001, such as at the distal end portion 1002 of the sleeve accessory 1001. The ribbed details 1010 may provide a surface for other components to attach to an end of the sleeve accessory 1001, such as via threaded, frictional or other engagement means. In some embodiments, the ribbed details 1010 may lift tissue of the patient away from a surface of the sleeve accessory 1001 when inserted into the patient. In some embodiments, the ribbed details 101 may beneficially help limit movement of the sleeve accessory 1001 (and speculum 200) when inserted into the patient.

As shown in FIGS. 8A-8L, the ribbed details 1010 may have a generally convex shape. For example, the ribbed details 1010 may extend outwardly from the exterior surface of the sleeve accessory 1001. In some embodiments, the ribbed details 1010 may have a concave shape. For example, FIGS. 8K-8O illustrate an example of the sleeve accessory 100 in which the ribbed details 1007 have a concave shape that extends inwardly towards the lumen of the sleeve accessory 1001.

The ribbed details may instead be, or may be combined with, texture differences or lubrication differences provided on an inner surface of the sleeve accessory 1001 and/or gripping elements positioned on an inner surface of the sleeve accessory 1001 that may help the sleeve accessory 1001 remain securely fastened onto the insertion portion 211 and/or the applicator 900. For example, the sleeve accessory 1001 may include one or more gripping elements 1005 positioned on an inner surface of the sleeve accessory 1001. The gripping elements 1005 may extend longitudinally from the proximal end 1004 of the sleeve accessory 1001 towards the distal end 1002 of the sleeve accessory 1001. The gripping elements 1005 may help the sleeve accessory 1001 remain securely fastened onto the insertion portion 211 of the speculum 200 and/or the applicator 900. As explained below, the gripping elements 1005 may provide at least some resistance to the applicator 900 being slid out from the sleeve accessory 1001 to help minimize unwanted slippage between the applicator 900 and the sleeve accessory 1001 and reduce the likelihood that the applicator 900 will unintentionally separate from the sleeve accessory 1001.

FIGS. 8A and 8B illustrate the sleeve accessory 1001 in the unexpanded or uncompressed position. The cylindrical body of the sleeve accessory 1001 may have a uniform width or diameter between the distal end of the sleeve accessory 1001 and the proximal end of the sleeve accessory while the sleeve accessory 1001 is in the unexpanded or uncompressed position, to match a uniform width or diameter of the bills 203 and 205 extending away from the handle 207. In some embodiment, the uniform diameter of the cylindrical body of the sleeve accessory 1001 may range between 0.25 inches and 3.0 inches. In other embodiments, the sleeve accessory 1001 may comprise a different natural shape than the shape of the bills 203 and 205, and may also have a non-uniform width or diameter ranging between 0.25 and 3.0 inches when in an un-stretched or unexpanded state.

As shown in FIGS. 8A-8B and 8Q-8R, the sleeve accessory 1001 in at least the unexpanded or uncompressed position may include a flared portion 1020 at the proximal end 1004 and an elongated portion 1022 extending from the proximal end 1004 to the distal end 1002 of the sleeve accessory 1001. The flared portion 1020 may be flared radially outwardly and towards the proximal end 1004 to provide a wider opening to correspond to a wider portion of the applicator 900 and/or the bills 203, 205. FIGS. 8Q and 8R illustrate an example of the sleeve accessory 1001 including a flared portion 1020 that flares radially outwardly a greater distance than the flared portion 1020 of the sleeve accessory shown in FIGS. 8A and 8B. The wider flared portion 1020 shown in FIGS. 8Q and 8R may be configured to surround a larger portion of the speculum 200 in use, providing additional comfort to the patient.

Figure 12A:
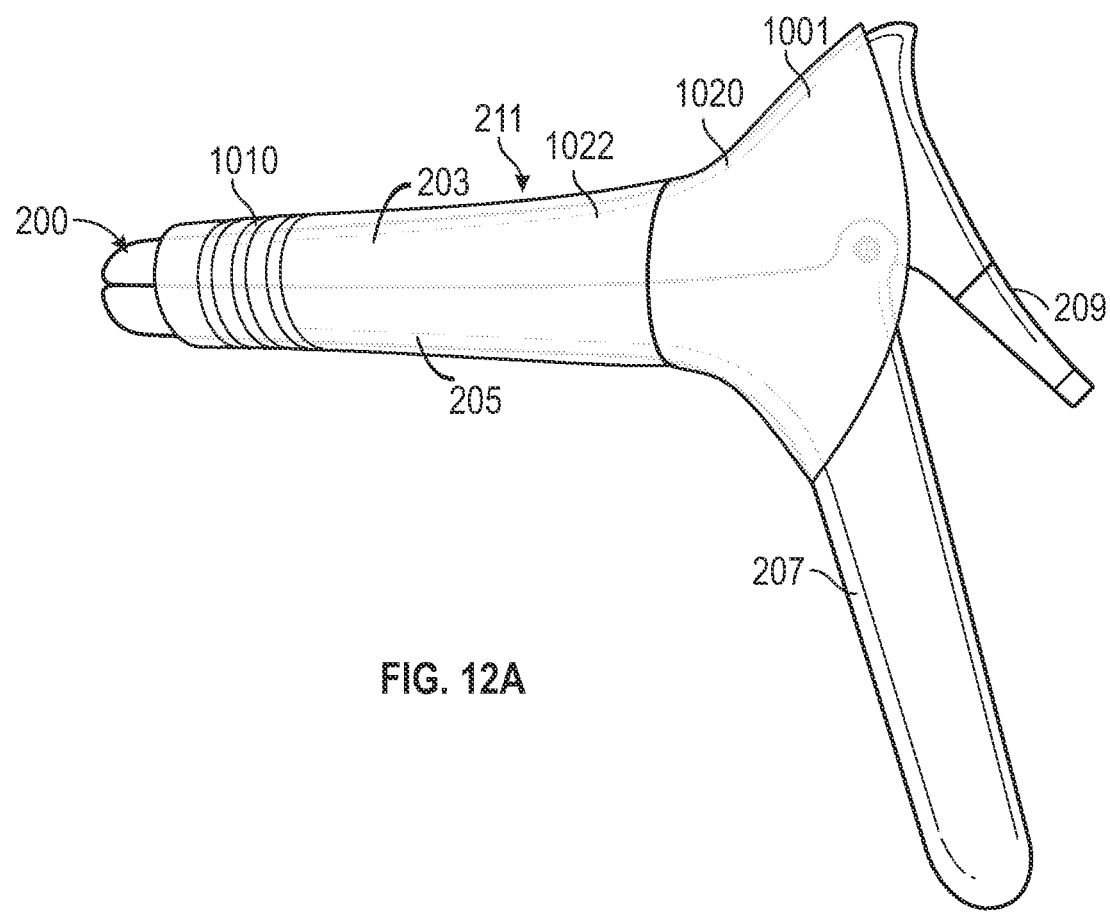
FIG. 12A is a side view of the sleeve accessory positioned on a medical speculum, according to one embodiment.
Figure 12B:
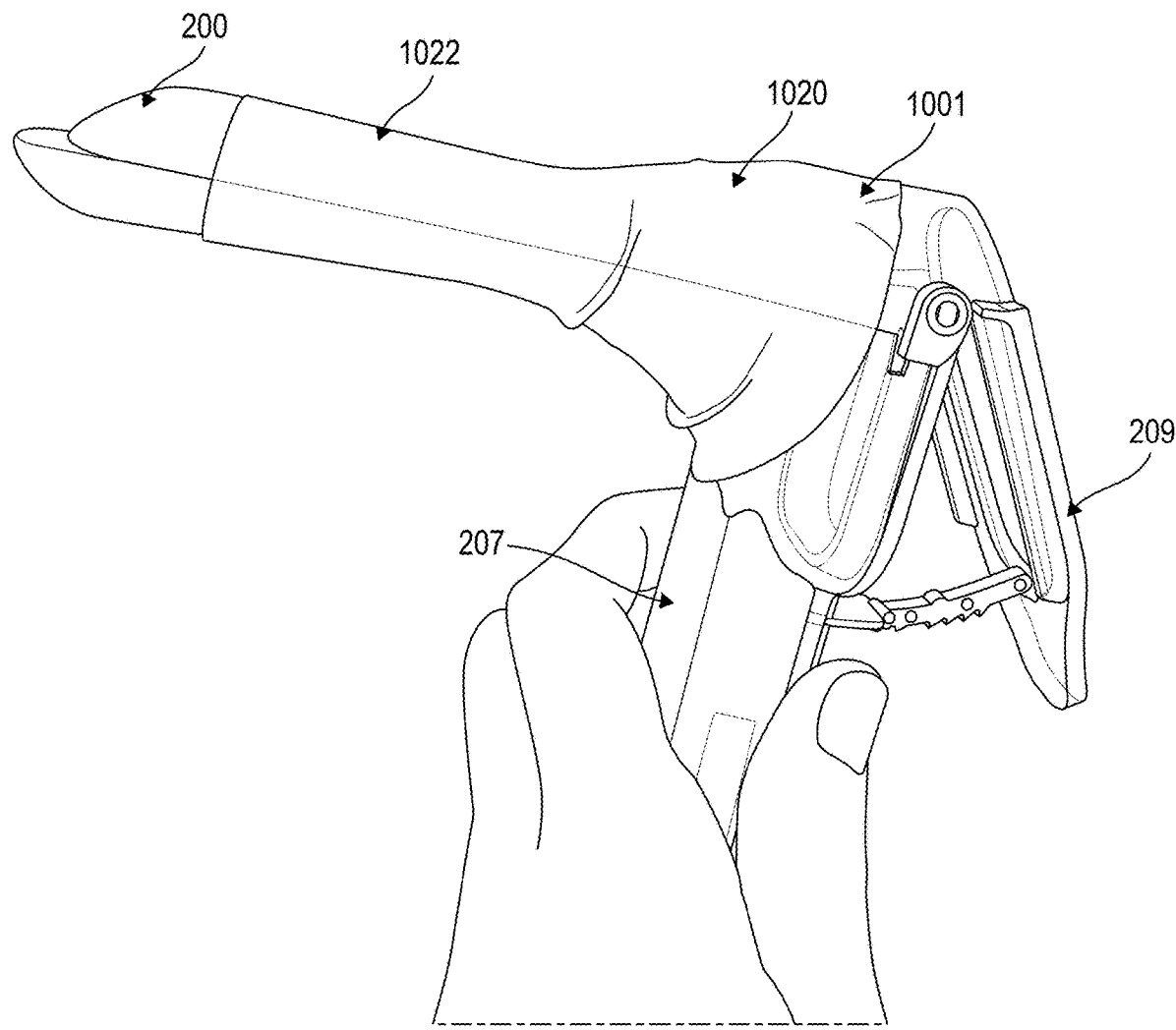
FIG. 12B is a side view of a sleeve accessory positioned on a medical speculum, according to one embodiment.

For example, FIG. 12A illustrates an example of the sleeve accessory 1001 positioned on the speculum 200. As shown, the flared portion 1020 of the sleeve accessory has a width or diameter that is wider than a width or diameter of the elongate portion 1022. The flared portion 1020 may beneficially flare radially outwardly from the elongate portion 1022 in a proximal direction to cover one or more portions of the speculum 200 to protect the patient from the one or more portions of the speculum 200. The flared portion 1020 (and/or other portions of the sleeve accessory 1001) may expand to conform to the shape of the one or more portions of the speculum 200 on which the sleeve accessory 1001 is positioned. The flared portion 1020 of the sleeve accessory 1001 may help to protect the patient from pinching by covering at least a hinged area of the speculum, which can often catch tissue or pubic hair, causing discomfort. Thus, at least the flared portion 1020 can help to reduce patient discomfort when the sleeve accessory and speculum are inserted into the patient.

The elongated portion 1022 of the sleeve accessory 1001 smoothly transitions from and extends from the flared portion 1020 to the distal end 1002 of the sleeve accessory 1001. The elongated portion 1022 may become be tapered and become more narrow as the elongated portion 1020 extends towards the distal end 1002 and/or may have a uniform width or diameter as the elongated portion 1020 extends towards the distal end 1002 to conform to the shape of the bills 203, 205.

FIGS. 8C-8F illustrate an example of the sleeve accessory 1001 in a compressed position. The sleeve accessory 1001 may be in the compressed position when the applicator 900 is positioned within the sleeve accessory 100. In some embodiments, insertion of the applicator 900 into the sleeve accessory 1001 causes the sleeve accessory 1001 to move from the uncompressed position to the compressed position. For example, insertion of the applicator 900 into the sleeve accessory 1001 may cause sides of the sleeve accessory 1001 to move radially outwardly and the top and bottom of the sleeve accessory to move radially inwardly towards one another. In some embodiments, the sleeve accessory 1001 may be preformed in the compressed position in which the sides of the sleeve accessory 1001 move radially outwardly and the top and bottom of the sleeve accessory 1001 moves radially inwardly towards one another, before the applicator 900 is inserted into the sleeve accessory 1001. As shown from FIG. 8F, in the compressed position, the sides of the sleeve accessory 1001 may be tapered inwardly from the proximal end 1004 to the distal end 1002. In some embodiments, in the compressed position, the top and bottom of the sleeve accessory 1001 may be tapered outwardly from the proximal end 1004 to the distal end 1002.

For example, in some embodiments, the flared portion 1020 of the sleeve accessory 1001 has a first length in the uncompressed position and the flared portion 1020 of the sleeve accessory 1001 has a second length in the compressed position. The second length may be greater than the first length. For example, in the uncompressed positon, the flared portion 1020 may extend distally from the proximal end 1004 along a portion of the length of the sleeve accessory 1001. In the compressed position, the flared portion 1020 may extend distally from the proximal end 1004 along a greater length of the sleeve accessory 1001.

FIGS. 9A-9F illustrate an example of the applicator 900 coupled with the sleeve assembly 1001. For example, the sleeve assembly 1001 may surround at least a portion of the applicator 900 and at least a portion of the applicator 900 may be positioned within the sleeve assembly 1001 (e.g., within an interior volume of the sleeve assembly 1001).

As illustrated in FIGS. 9A-9F, the applicator 900 is positioned within the sleeve accessory 1001. The applicator 900 and the sleeve accessory 1001 may be packaged together with the applicator 900 and pre-inserted into the sleeve accessory 1001 or in some embodiments, the applicator 900 may be slid into or otherwise be positioned within the sleeve accessory 1001 by the user. In some embodiments, the applicator 900 is designed such that the oblong shape of the applicator 900, with the broader proximal end 902 narrowing to the distal end 904, conforms to and/or otherwise fits the shape of the sleeve accessory 1001, which may also narrow in width from the broader proximal end 1002 to the narrower distal end 1004. Accordingly, the applicator 900 may be easily positioned within the sleeve accessory 1001 for a distance until the prongs 908 and 910 abut the walls of the sleeve accessory 1001. In some embodiments, insertion of the applicator 900 into the sleeve accessory 1001 may cause sides of the sleeve accessory 1001 to move radially outwardly and the top and bottom of the sleeve accessory to move radially inwardly towards one another. In some embodiments, the sleeve accessory 1001 may be preformed in the compressed position in which the sides of the sleeve accessory 1001 move radially outwardly and the top and bottom of the sleeve accessory 1001 moves radially inwardly towards one another, before the applicator 900 is inserted into the sleeve accessory 1001.

In some embodiments, the prongs 908, 910 may beneficially create friction between the applicator 900 and walls of the sleeve accessory 1001 such that there is at least some resistance to the applicator 900 being slid out from the sleeve accessory 1001. This helps minimize unwanted slippage between the applicator 900 and the sleeve accessory 1001, such that there is a reduced likelihood the applicator 900 will unintentionally separate from the sleeve accessory 1001.

As mentioned above, the sleeve accessory 1001 may include one or more gripping elements 1005. The gripping elements 1005 may additionally help the sleeve accessory 1001 remain securely fastened onto the insertion portion 211 of the speculum 200. The gripping elements 1005 may provide at least some resistance to the applicator 900 being slid out from the sleeve accessory 1001 to help minimize unwanted slippage between the applicator 900 and the sleeve accessory 1001 and reduce the likelihood that the applicator 900 will unintentionally separate from the sleeve accessory 1001.

Additionally, the tab 906 is configured to be folded over a top edge (e.g., over the end ring 1009) of the proximal end 1002 of the sleeve accessory 1001 once the applicator 900 has been slid or otherwise positioned into the sleeve accessory 1001. When the applicator 900 is positioned at least partially within the sleeve accessory 1001, the tab proximal end 1002 of the sleeve accessory 1001 may be seated as far under the 906 as possible (e.g., the proximal end of the sleeve accessory 1001 abuts a portion of the tab 906 that connects to the applicator body). Thus, the tab 906 and/or the resistance created by friction between the prongs 908 and 910 and the walls of the sleeve accessory 1001 may prevent or limit the applicator 900 from inadvertently sliding out of the sleeve accessory 1001. Instead, once the applicator 900 is inserted into the sleeve accessory 1001, at least a small force may need to be applied to remove the applicator 900 from the sleeve accessory 1001.

Additionally, the prongs 908 and 910 are configured such that when the applicator 900 is inserted into the sleeve accessory 1001, the prongs 908 and 910 hold the interior of the sleeve accessory 1001 at least partially open. In this way, the prongs 908 and 910 allow a user to easily slide an insertion portion of a medical speculum into the interior of sleeve accessory 1001. In some examples, the prongs 908, 910 may optionally each include respective slits 909, 911 formed at the distal end of each of the prongs 908, 910 when the applicator 900 is in the folded position. As mentioned above, the slits 909, 911 may be formed along the fold lines 916, 918 when the applicator 900 is in the folded position. In some embodiments, the applicator 900 does not include slits 909, 911 and folds entirely along the fold lines 916, 918 (e.g., see FIG. 7G). The slits 909, 911 define the space between the main body 901 of the applicator 900 and the flaps 912, 914. The slits 909, 911 and/or the folded prongs 908, 910 (and flaps 912, 914) may cause a spring-like effect such that the flaps 912, 914 deflect when a force is applied to the flaps. For example, the flaps 912, 914 may deflect inwardly into the slits 909, 911 towards the main body 901 of the applicator 900. Such configurations may help to hold the interior of the sleeve accessory 1000 at least partially open to allow for easier application of the sleeve accessory 1001 to the speculum 200, such as by the applicator 900. Thus, even in embodiments of the applicator 900 in which the applicator is a generally rigid structure, the applicator 900 allows for the sleeve accessory 1001 to remain expanded to be applied to the speculum.

In some embodiments, the prongs 908, 910 are spaced apart such that the space between the first fold line 916 and the second fold line 918 are at least as wide as the insertion portion of the medical speculum. As such, the insertion portion may be slid in between the prongs 908, 910 and through the pockets 920 and 922 formed in the prongs 908, 910. Thus, the prongs 908, 910 of the applicator 900 may guide the insertion portion of the medical speculum into the lumen of sleeve accessory 1001.

As shown in FIGS. 9A-9F, in some embodiments, the distal ends 904 of the prongs 908, 910 may not reach the distal end 1004 of the sleeve accessory 1001. However, in other embodiments, the applicator 900 may be configured such that the ends of the prongs 908, 910 meet the distal end 1004 of the sleeve accessory 1001, or the applicator 900 may be configured such that the ends of the prongs 908, 910 extend past the distal end 1004 of the sleeve accessory 1001.

Figure 10B:
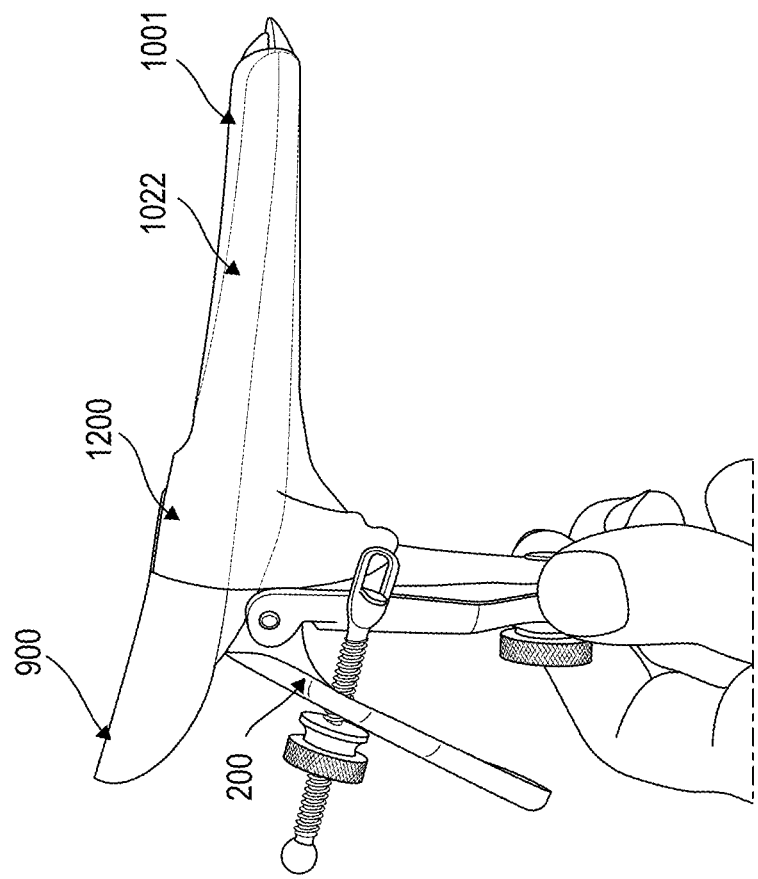
FIG. 10B is a side view of an applicator-sleeve accessory assembly positioned on a medical speculum, according to an example embodiment.
Figure 10A:
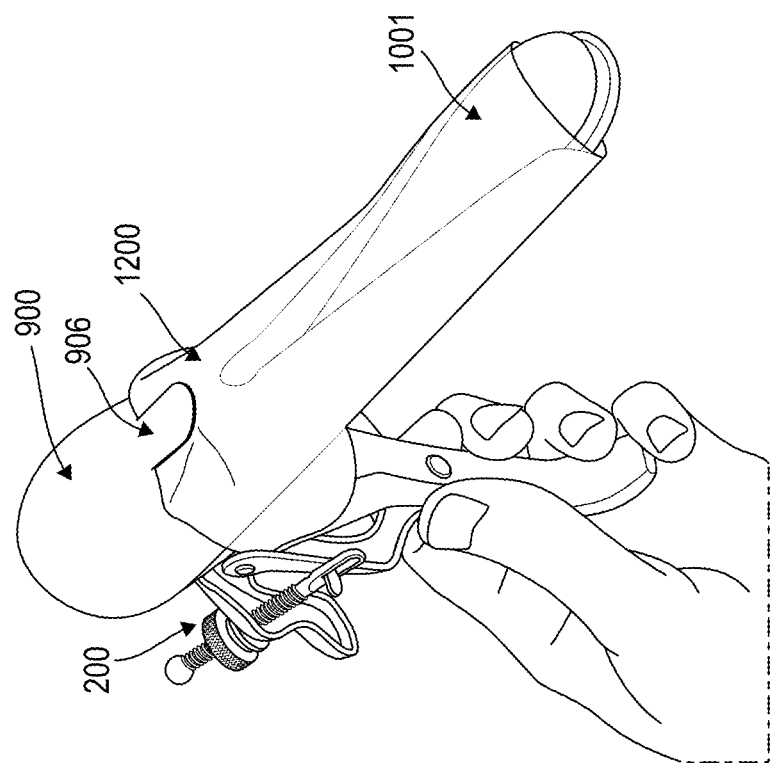
FIG. 10A is a perspective view of an applicator-sleeve accessory assembly positioned on a medical speculum, according to an example embodiment.
Figure 10D:
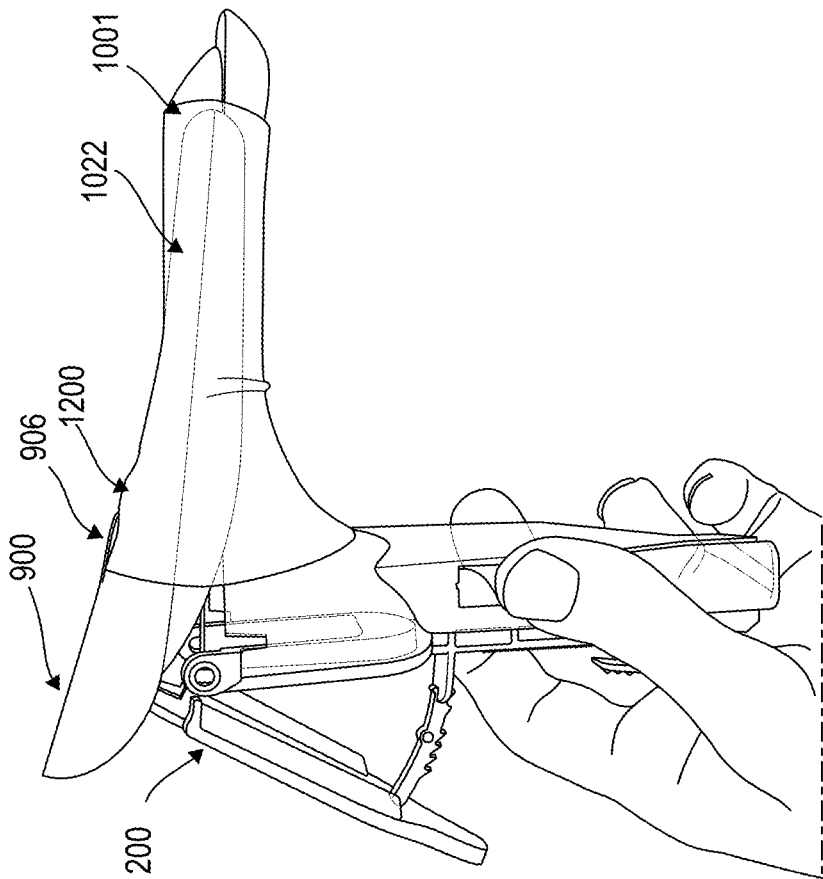
FIG. 10D is a side view of an applicator-sleeve accessory assembly positioned on a medical speculum, according to an example embodiment.
Figure 10C:
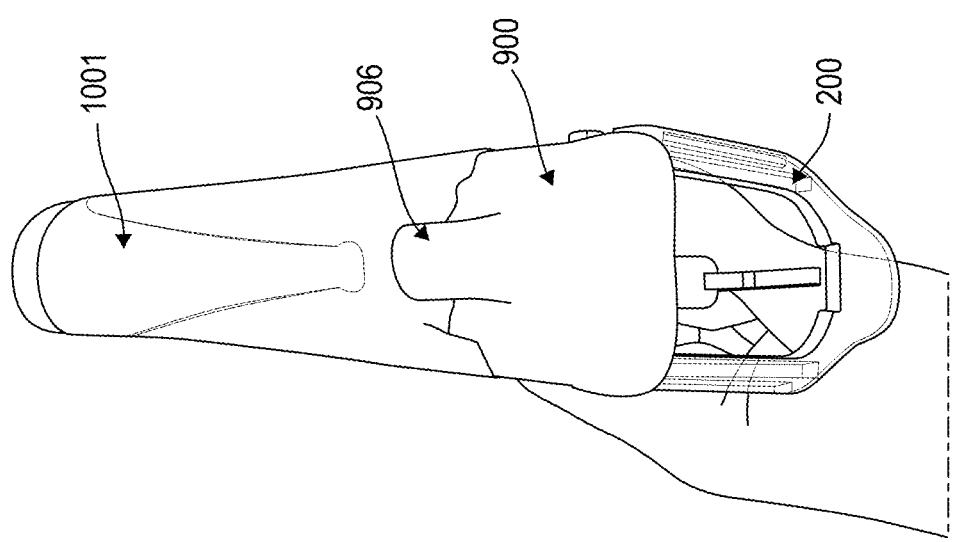
FIG. 10C is a perspective view of an applicator-sleeve accessory assembly positioned on a medical speculum, according to an example embodiment.

FIGS. 10A-10D illustrate an example of the assembly of the applicator 900 positioned at least partially within sleeve accessory 1001, positioned on a medical speculum 200, before the applicator 900 is removed from the speculum 200. FIGS. 10A-10B illustrate an example of the applicator-sleeve accessory assembly positioned on an example of a speculum of a first material, such as metal. FIGS. 10C-10D illustrate an example of the applicator-sleeve accessory assembly positioned on an example of a speculum of a second material, such as plastic. As shown in this position, sides of the bills of the speculum 200 or other portions of the speculum are positioned in the pockets 920, 922 formed in the prongs 908, 910 of the applicator 900. Thus, the pockets 920, 922 form a receiving space for the speculum and helps to separate the speculum from the sleeve accessory 1001 when the sleeve accessory 1001 is applied to the speculum. Such configurations may help to improve the application process for applying the sleeve accessory 1001 to the speculum 200, at least in part, by reducing or limiting the sleeve accessory 1001 from getting caught on the speculum 200.

The tab 906 secures the sleeve accessory 1001 to the applicator 900 at the proximal end of the sleeve accessory 1001. At least a portion of the proximal end of the sleeve accessory 1001 is positioned within the receiving space formed between the tab 906 and the main body 903 of the applicator 900 and may abut at least a portion of the applicator formed at the connection between the tab 906 and the main body 903.

As shown in FIGS. 10A-10D, when the applicator-sleeve accessory assembly is positioned on the speculum 200, the prongs 908-910 of the applicator 900 cause at least a portion of the elongate portion 1022 of the sleeve accessory 1001 to expand to accommodate the shape of the insertion portion 211 and/or the bills of the speculum 200. As shown, in this position, the flared portion 1020 of the sleeve accessory 1001 surrounds at least a portion of the applicator 900, and surrounds at least a portion of the speculum 200, such as at least a portion of the handle 207 of the speculum 200. Thus the applicator 900 may position the sleeve accessory 1001 around one or more portions of the speculum 200 that may be more prone to causing discomfort to the patient, such as around the bills of the speculum, the handle 207, or a hinged portion of the speculum 200 and/or the like.

The proximal end of the applicator 900 may extend proximally beyond the handle 207 of the speculum or a proximal end of the bills of the speculum. Such configurations may allow the applicator 900 to be easily gripped by the user and/or removed from the sleeve accessory 1001 and/or speculum.

FIGS. 11A-11D illustrate a process of using the applicator 700 to position the sleeve accessory 801 on a medical speculum, such as speculum 200. Although the applicator 700 and the accessory 801 are illustrated, any of the other example applicators (e.g., applicator 700, 900), and sleeve accessories (e.g., sleeve accessory 301, 501, 601, 801, 1001) described herein may be used in a similar manner and process. First, the user removes an applicator 700 and a sleeve accessory 801 from packaging. In some embodiments, the applicator 700 and the sleeve accessory 801 may be sterilized in the package, or later after the applicator 700 and the sleeve accessory 801 are unpackaged. In exemplary embodiments, the applicator 700 and the sleeve accessory 801 are packaged together with the applicator 700 pre-inserted into the sleeve accessory 801 (e.g., as shown in FIG. 6C). In such embodiments the user may, for example, remove the applicator 700 and sleeve accessory 801 combination from the packaging by grasping the broad, proximal end 702 of the applicator and pulling the applicator 700 and sleeve accessory 801 combination from the packaging. In this way, the user may remove the applicator 700 and sleeve accessory 801 from the packaging without directly handling the sleeve accessory 801, which may help keep the sleeve accessory 801 sterile. However, in other embodiments, the applicator 700 and the sleeve accessory 801 may be packaged in separate packaging or may be packaged together but without the applicator 700 pre-inserted into the sleeve accessory 801. In such embodiments, the user may remove the applicator 700 and the sleeve accessory 801 from the packaging and insert the applicator 700 (e.g., by the distal end 704 of the applicator 700) at least partially into the sleeve accessory 801, as shown in FIG. 6C.

Figure 11A:
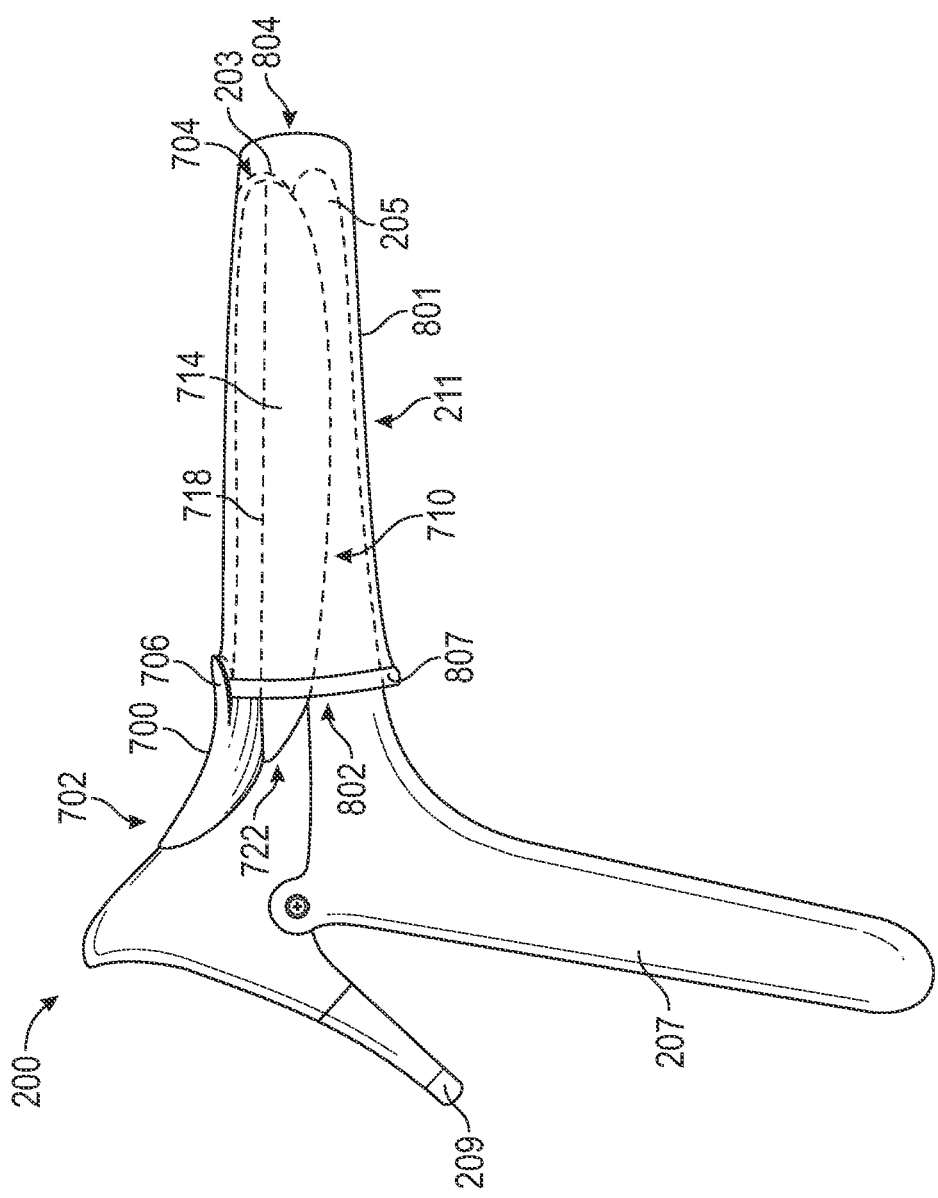
FIG. 11A is a side view of the applicator of FIGS. 6A-6C being used to position a sleeve accessory on a medical speculum, according to an example embodiment.
Figure 11B:
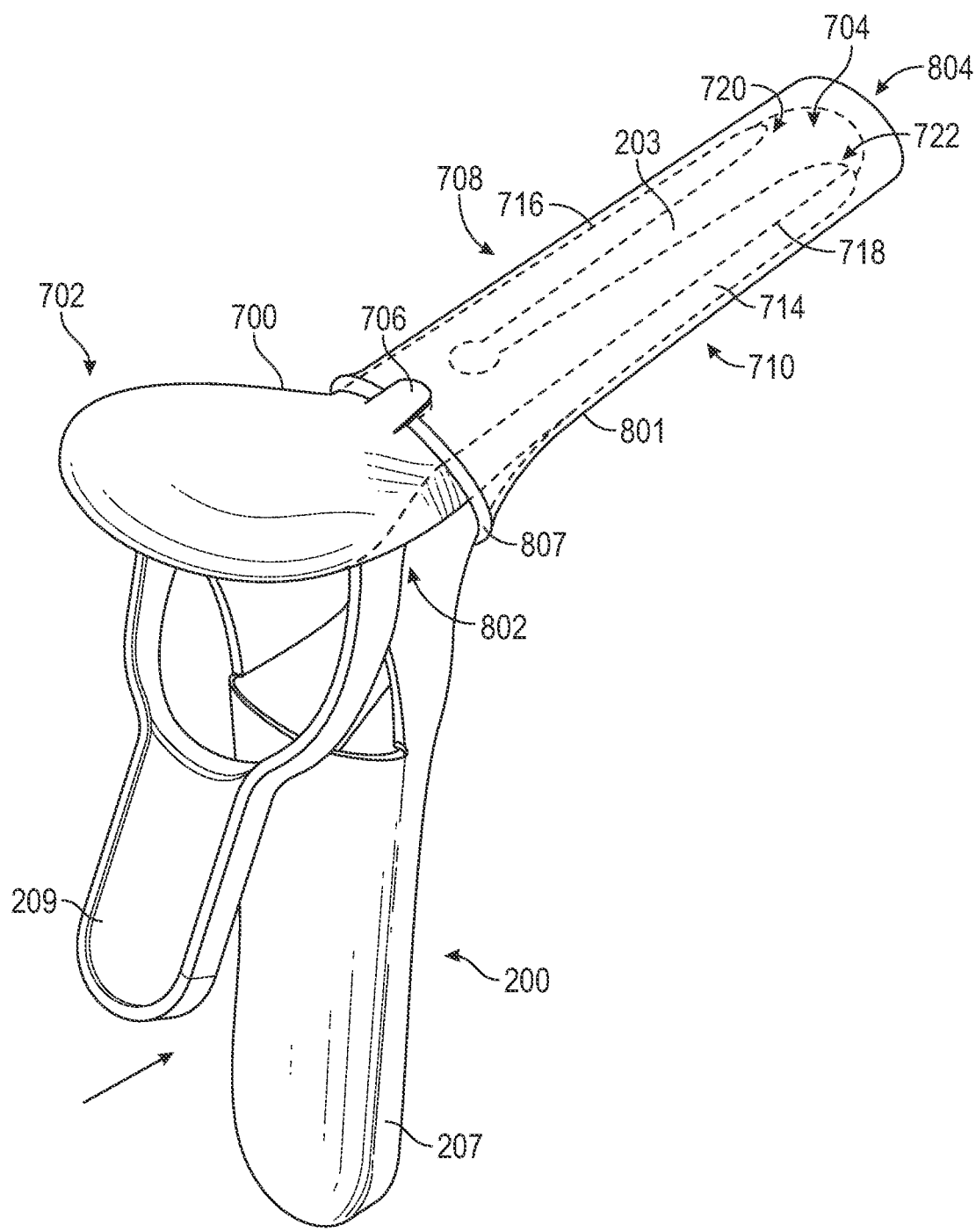
FIG. 11B is a top perspective view of the applicator of FIGS. 6A-6C being used to position a sleeve accessory on a medical speculum, according to an example embodiment.

With the applicator 700 positioned in the sleeve accessory 801, the prongs 708 and 710 of the applicator 700 hold the interior of the sleeve accessory 801 at least partially open. Further, the applicator 700 should not inadvertently slide out of the sleeve accessory 801 once inserted into the sleeve accessory 801. Thus, the user then grasps the applicator 700 by the broad, proximal end 702, thereby holding the sleeve accessory 801. Next, holding the speculum 200 by the handle 207, the user inserts the insertion portion 211 of the speculum 200 into the lumen of the sleeve accessory 801 through the proximal end 802 of the sleeve accessory 801. FIGS. 11A and 11B illustrate the insertion portion 211 of the speculum 200 being inserted into the sleeve accessory 801, with FIG. 11A showing a side view of the speculum 200 being inserted into the sleeve accessory 801 and FIG. 11B showing a top perspective view of the speculum 200 being inserted into the sleeve accessory 801. In FIGS. 11A and 11B, the speculum 200 is inserted by pushing the sliding the speculum 200 into the sleeve accessory 801 in the direction of the arrows shown in FIGS. 11A and 11B. Further, as shown in FIGS. 11A and 11B, the applicator 700 is designed such that the insertion portion 211 may be inserted in between the prongs 708 and 710 and through the pockets 720 and 722 created by the prongs 708 and 710, such that the flaps 712 and 714 envelop the sides of the bills 203 and 205 once speculum 200 is inserted.

Figure 11C:
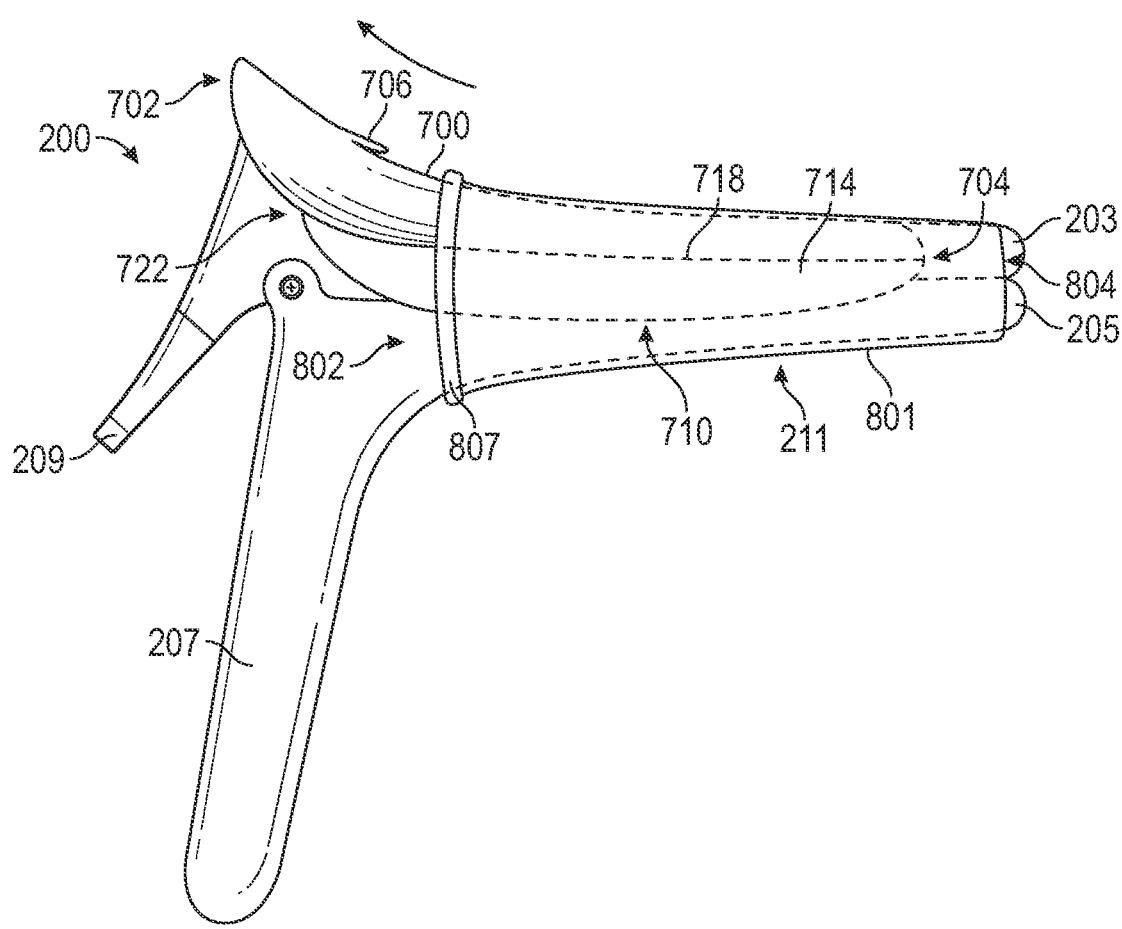
FIG. 11C is a side view of the applicator of FIGS. 6A-6C being used to position a sleeve accessory on a medical speculum, according to an example embodiment.
Figure 11D:
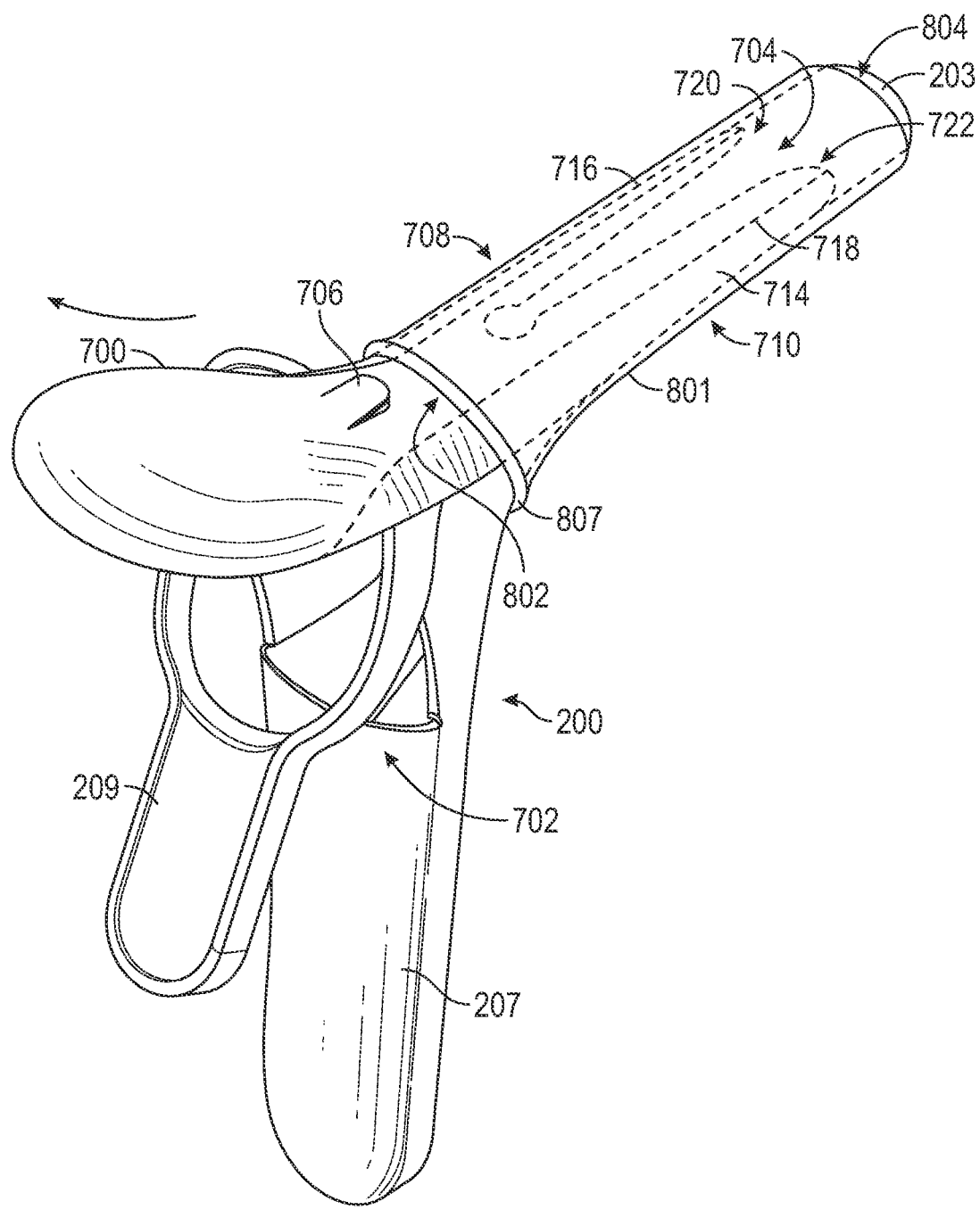
FIG. 11D is a top perspective view of the applicator of FIGS. 6A-6C being used to position a sleeve accessory on a medical speculum, according to an example embodiment.
Figure 11E:
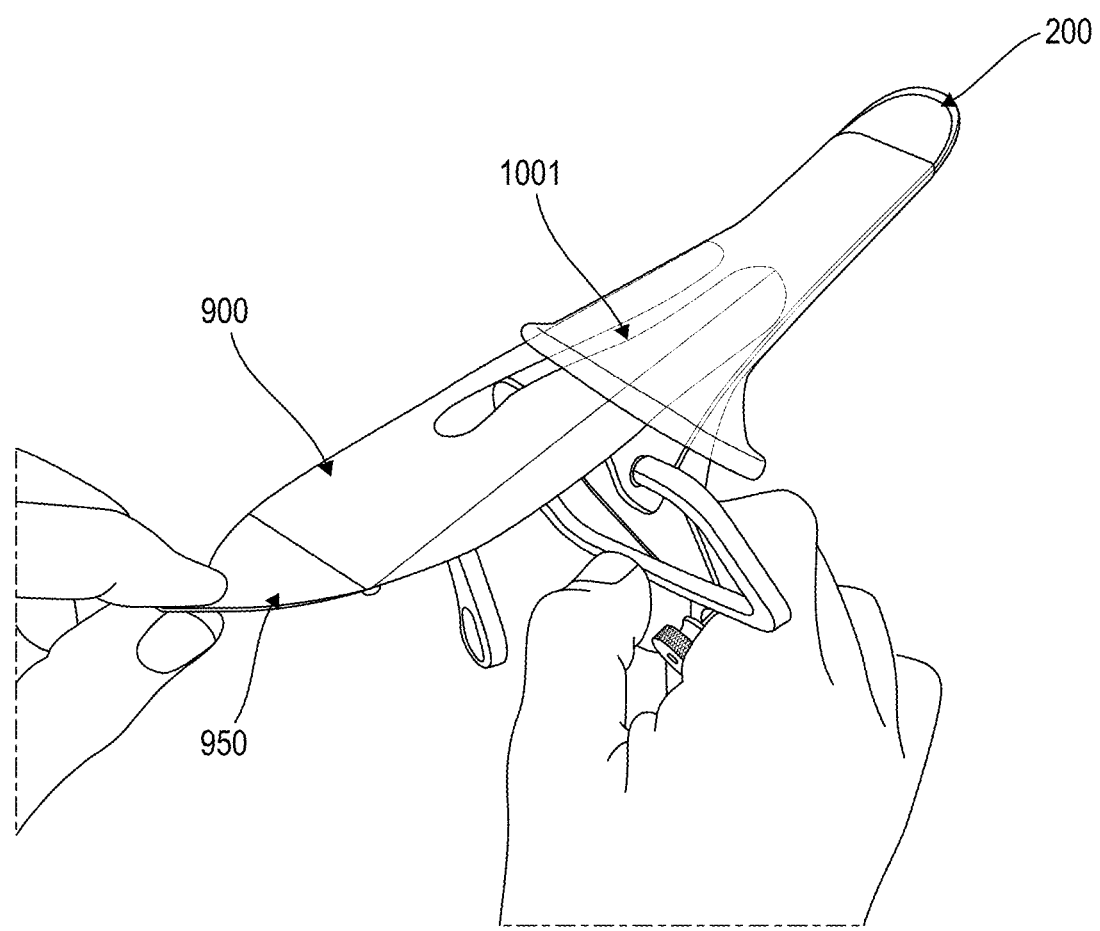
FIG. 11E is a top perspective view of an applicator being used to position a sleeve accessory on a medical speculum, according to an example embodiment.

Once the insertion portion 211 has been inserted into the lumen of the sleeve accessory 801, the user grasps the proximal end 702 of the applicator 700 and, still holding the speculum 200 by the handle 207, pulls the applicator 700 out from the lumen of the sleeve accessory 801. FIGS. 11C and 11D illustrate the applicator 700 being removed from the sleeve accessory 801, with FIG. 11C showing a side view of the speculum 200 with the applicator 700 being removed and FIG. 11D showing a top perspective view of the speculum 200 with the applicator 700 being removed. The applicator 700 is removed in the direction of the arrows shown in FIGS. 11C and 11D. As discussed above, once inserted into the sleeve accessory 801, friction may exist between the prongs 708 and 710 of the applicator 700 and the walls of the sleeve accessory 801. Thus, when the applicator 700 is removed from the sleeve accessory 801, this friction may pull the sleeve accessory 801 more fully and more securely onto the insertion portion 211 of the speculum 200. For example, by comparing FIGS. 11A and 11B with FIGS. 11C and 11D, one can see that the act of pulling the applicator 700 out from the sleeve accessory 801 has caused the distal end 804 of the sleeve accessory 801 to be pulled past the distal ends of the bills 203 and 205. The user continues to pull the applicator 700 until it is completely removed from the sleeve accessory 801, at which point the sleeve accessory 801 is fully positioned on the insertion portion 211 of the speculum 200. In some embodiments, such as the example shown in FIG. 11E, the user pulls on a tabbed portion 950 of the applicator 900 to remove the applicator 900 from the sleeve accessory 801.

FIGS. 12A-12F illustrate examples of the sleeve accessory 1001, once the sleeve accessory 1001 has been positioned on the speculum 200. As mentioned above, as shown in FIG. 12A and FIG. 12B, the flared portion 1020 may beneficially flare radially outwardly from the elongate portion 1022 in a proximal direction to cover one or more portions of the speculum 200 to protect the patient from the one or more portions of the speculum 200. The flared portion 1020 (and/or other portions of the sleeve accessory 1001) may expand to conform to the shape of the one or more portions of the speculum 200 on which the sleeve accessory 1001 is positioned. The flared portion 1020 of the sleeve accessory 1001 may help to protect the patient from pinching by covering at least a hinged area of the speculum, which can often catch tissue or pubic hair, causing discomfort. Thus, at least the flared portion 1020 can help to reduce patient discomfort when the sleeve accessory and speculum are inserted into the patient.

Figure 12D:
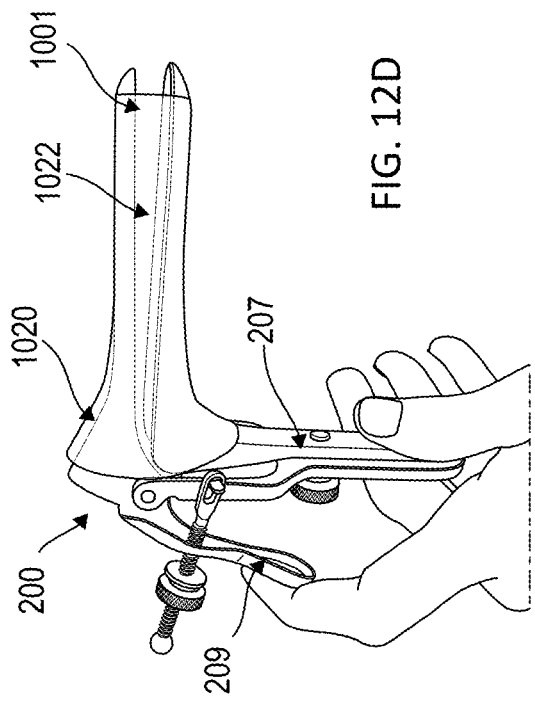
FIG. 12D is a perspective view of a sleeve accessory positioned on a medical speculum, in a second position, according to one embodiment.
Figure 12F:
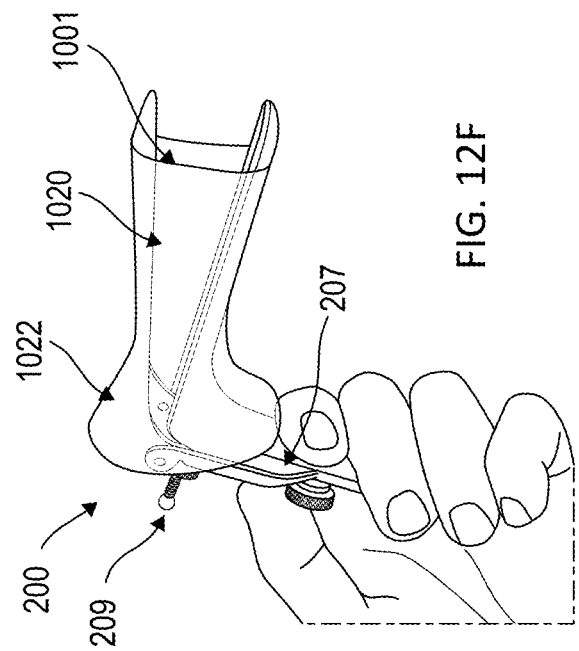
FIG. 12F is a perspective view of a sleeve accessory positioned on a medical speculum, in a fourth position, according to one embodiment.
Figure 12C:
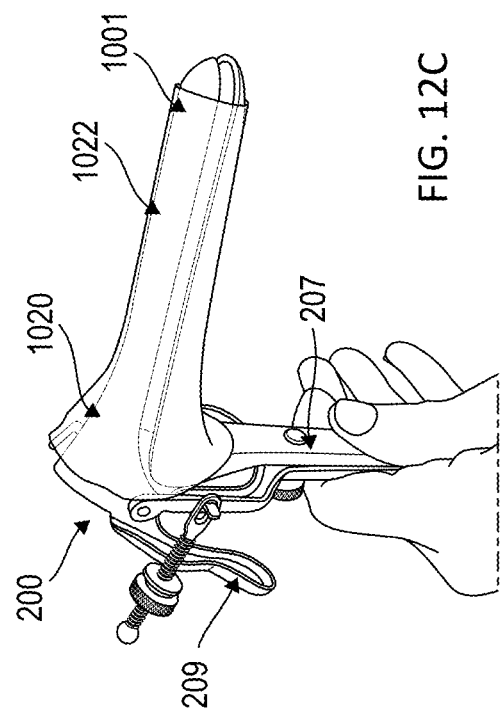
FIG. 12C is a perspective view of a sleeve accessory positioned on a medical speculum, in a first position, according to one embodiment.
Figure 12E:
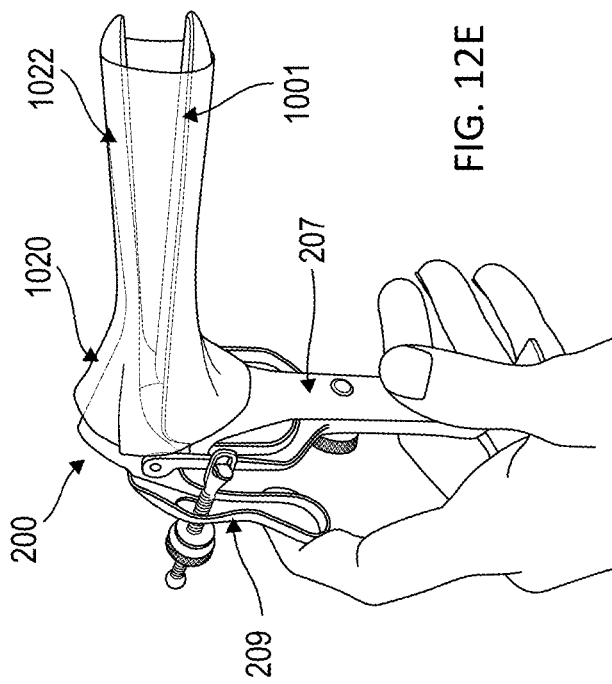
FIG. 12E is a perspective view of a sleeve accessory positioned on a medical speculum, in a third position, according to one embodiment.

FIGS. 12C-12F illustrate various configurations of the sleeve accessory 1001 positioned on the speculum 200 when the handle 207 and/or the lever 209 of the speculum 200 is activated, causing at least a portion of the sleeve accessory 1001, such as the elongate portion 1022, to expand. For example, FIG. 12C illustrates the sleeve accessory 1001 in a first position. As shown the elongate portion 1022 of the sleeve accessory 1001 conforms to the shape of the bills of the speculum 200. In FIGS. 12D and 12E, the handle 207 and/or the lever 209 are actuated, such that depression of the lever 209 towards the handle 207 (or vice versa) causes the bills of the speculum 200 to pivot away from one another into a second position (see FIG. 12D) and a third position (see FIG. 12E). Pivoting of one or more of the bills of the speculum 200 causes at least the elongated portion 1022 of the sleeve accessory 1001 to expand or stretch. FIG. 12F shows an example of the bills of the speculum 200 and the sleeve accessory 1001 in a fourth position, in which the handle 207 and/or the lever 209 have been actuated by a maximum distance. Thus, in the fourth positon, the elongate portion 1022 of the sleeve accessory 1001 is stretched by a maximum or near maximum distance, as the sleeve accessory 1001 conforms to the shape of the speculum 200. Stretching the sleeve accessory 1001 may increase visibility and access to the cervix, by, for example, retracting encroaching vaginal sidewall tissue. The sleeve accessory 1001 described herein helps to improve patient comfort, at least in part by protecting the vaginal sidewalls of the patient, and minimizing pinching risk. The sleeve accessory 1001 also may allow for a smaller and more comfortable speculum to be used, as the sleeve accessory 1001 expands to provide a channel for access to the cervix or other vaginal tissue. The sleeve accessory 100 may separate the speculum from the patient's tissue, thereby reducing a cold sensation caused to the patient by the speculum.

In some embodiments, an applicator (e.g., applicator 700, 900), a sleeve accessory (e.g., sleeve accessory 301, 501, 601, 801, 1001), and/or a medical speculum (e.g., speculum 200) may be provided in a kit form. In one embodiment, the kit may include one applicator, one accessory sleeve, and/or one speculum. In another embodiment, the kit may include a plurality of speculums of varying lengths and widths and of varying expansion capabilities (i.e., capable of opening the bills in different ways, to different opening lengths, etc.), one or more sleeves configured to fit the plurality of speculums, and one or more applicators configured to fit the one or more sleeves and position the one or more sleeves on the one or more speculums. In some embodiments, the kit includes the applicator and the sleeve accessory in which the applicator is already positioned at least partially within the sleeve accessory. In yet another embodiment, the kit may further include accessories related to the needs of the examination procedure, for example, an IUD insertion device, a disposable electrosurgery tool, etc. In yet another embodiment, a plurality of applicators can be provided loosely in a large package or box.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the technology should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims are generally intended as "open" terms (e.g., the term "including" should be interpreted as "including but not limited to," the terms "comprising" and "having" should, respectively, be interpreted as "comprising at least" and "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an." In general, "a" and/or "an" should be interpreted to mean "at least one" or "one or more"; the same holds true for the use of definite articles used to introduce claim recitations.

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The technology disclosed herein has numerous applications and while particular embodiments of the technology have been described in detail, it will be apparent to those skilled in the art that the disclosed embodiments may be modified given the design considerations discussed herein. Therefore, the foregoing description is to be considered exemplary rather than limiting, and the true scope of the invention is that defined in the following claims.

What is claimed is:

1. A kit comprising:
a sleeve accessory having a sleeve body defining a lumen that extends from a proximal end to a distal end of the sleeve body, wherein the sleeve body extends continuously between the proximal end of the sleeve body and the distal end of the sleeve body, wherein the sleeve accessory is configured to be positioned on an insertion portion of a medical speculum, wherein the sleeve accessory is configured to be positioned on an insertion portion of a medical speculum, and wherein a circumference of the proximal end of the sleeve body is larger than a circumference of the distal end of the sleeve body when the sleeve accessory is not positioned on an insertion portion of a medical speculum; and
an applicator having a flat, oblong shape with a distal end and a proximal end, the proximal end being broader than the distal end;
wherein the distal end comprises a first prong and a second prong, wherein the first prong and the second prong of the applicator are configured to be folded into a first pocket and a second pocket, respectively; and
the first pocket and the second pocket are configured to receive the insertion portion of the medical speculum and thereby guide the insertion portion into the lumen of the sleeve accessory; and
wherein the applicator is configured to slide, by the distal end of the applicator, at least partially into the lumen of the sleeve accessory to facilitate positioning of the sleeve accessory on an insertion portion of a medical speculum.

2. The kit of claim 1, further comprising a medical speculum.

3. The kit of claim 1, wherein the first prong and the second prong are spaced apart such that, once the applicator has been slid at least partially into the lumen of the sleeve accessory, the first prong and the second prong abut walls of the sleeve accessory and create resistance to the applicator being removed from the sleeve accessory.

4. The kit of claim 1, wherein the applicator is disposable.

5. The kit of claim 1, wherein the applicator is made of a rubber, plastic, paper or cardboard material.

6. The kit of claim 1, further comprising a plurality of sleeve accessories.

7. The kit of claim 1, further comprising a plurality of applicators.

8. The kit of claim 1, further comprising a distal rib extending about at least a portion of the distal end of the sleeve body.

9. The kit of claim 8, wherein the distal rib has a concave shape.

10. The kit of claim 8, wherein the distal rib has a convex shape.

11. The kit of claim 1, further comprising a proximal rib extending about at least a portion of the proximal end of the sleeve body.

12. A method for positioning a sleeve accessory on a medical speculum, comprising:
providing a medical speculum with a pair of bills;
providing a kit of claim 1;
positioning the lumen of the sleeve accessory about the distal end of the applicator;
sliding the bills of the speculum between the first pocket and the second pocket of the applicator to position the bills of the speculum in the lumen of the sleeve accessory; and
removing the applicator from the lumen of the sleeve accessory.

13. The method of claim 12, wherein removing the applicator from the lumen of the sleeve accessory pulls the sleeve accessory further onto the bills of the medical speculum.

14. The method of claim 12, wherein:
positioning the lumen of the sleeve accessory about the distal end of the applicator comprises sliding the distal end of the applicator into the lumen of the sleeve accessory until the first prong and the second prong abut walls of the sleeve body of the sleeve accessory.

15. The method of claim 12, wherein the proximal end of the applicator includes a tab, and wherein the method further comprises tucking a proximal end of the accessory sleeve under the tab.

16. The method of claim 12, wherein positioning the lumen of the sleeve accessory about the distal end of the applicator is configured to cause sides of the sleeve accessory to stretch radially outwardly and a top and a bottom of the sleeve accessory to stretch radially inwardly.

17. The method of claim 12, wherein the applicator is made of a rubber, plastic, paper or cardboard material.

* * * * *